US012575714B2

(12) United States Patent
Sørensen et al.

(10) Patent No.: US 12,575,714 B2
(45) Date of Patent: Mar. 17, 2026

(54) TIP PART FOR FORMING A TIP OF A DISPOSABLE INSERTION ENDOSCOPE

(71) Applicant: AMBU A/S, Ballerup (DK)

(72) Inventors: Morten Sørensen, Ballerup (DK); Lasse Markworth Johnsen, Birkerød (DK)

(73) Assignee: AMBU A/S, Ballerup (DK)

( * ) Notice: Subject to any disclaimer, the term of this patent is extended or adjusted under 35 U.S.C. 154(b) by 413 days.

(21) Appl. No.: 17/794,699

(22) PCT Filed: Nov. 26, 2020

(86) PCT No.: PCT/EP2020/083527
§ 371 (c)(1),
(2) Date: Jul. 22, 2022

(87) PCT Pub. No.: WO2021/151552
PCT Pub. Date: Aug. 5, 2021

(65) Prior Publication Data
US 2023/0068676 A1      Mar. 2, 2023

(30) Foreign Application Priority Data

Jan. 28, 2020    (EP) ..................................... 20153967

(51) Int. Cl.
*A61B 1/00*        (2006.01)
*A61B 1/005*       (2006.01)
(Continued)

(52) U.S. Cl.
CPC ........ *A61B 1/0011* (2013.01); *A61B 1/00066* (2013.01); *A61B 1/00091* (2013.01);
(Continued)

(58) Field of Classification Search
CPC .............. A61B 1/0011; A61B 1/00066; A61B 1/00091; A61B 1/00096; A61B 1/015;
(Continued)

(56) References Cited

U.S. PATENT DOCUMENTS 5,257,617 A    11/1993  Takahashi
5,419,311 A     5/1995  Yabe et al.
(Continued)

FOREIGN PATENT DOCUMENTS

DE          3004089 A1    8/1980
EP          0161834 B1    1/1988
(Continued)

OTHER PUBLICATIONS

Examination Report issued for EP Patent Application No. 20153967. 3, dated Jan. 24, 2024, 5 pages.
(Continued)

*Primary Examiner* — Anh T Nguyen
*Assistant Examiner* — Li-Ting Song
(74) *Attorney, Agent, or Firm* — Faegre Drinker Biddle & Reath LLP

(57)                ABSTRACT

A tip part (2) for forming a tip of a disposable insertion endoscope (1), the tip part comprising an exterior housing (9) having an open proximal end (9a) for connection to other parts of the endoscope, the housing further having a distal front wall (11) and a circumferential housing wall (12), the circumferential housing wall extending a total housing length H in a proximal direction from the distal front wall to the proximal end of the housing, the distal front wall and the circumferential housing wall enclosing an interior spacing (24) of the tip part; a camera assembly able to provide an image from light received from an object to be investigated; and a tube insertion sleeve (38) provided within the interior spacing and fixed in relation to the distal front wall, the tube (Continued)

insertion sleeve being formed by a circumferential tube sleeve wall (39) that extends a total tube sleeve length S from the distal front wall of the housing to a proximal end of the tube insertion sleeve so that the tube insertion sleeve comprises an open proximal end; wherein the distal front wall has a fluid opening (10, 16a, 16b, 17) which is aligned with a distal end of the tube insertion sleeve, a proximal surface of the distal front wall surrounding the fluid opening to provide a tube abutment surface (40); whereby a tube (13, 21, 22, 23) can be inserted through the proximal end of the tube insertion sleeve until a distal end of the tube abuts the tube abutment surface, whereby the distal end of the tube is positioned to allow fluid flow through the tube to and through the fluid opening. Furthermore a method of manufacture of the tip part is disclosed.

21 Claims, 9 Drawing Sheets

(51) Int. Cl.

| | |
|---|---|
| *A61B 1/015* | (2006.01) |
| *A61B 1/018* | (2006.01) |
| *A61B 1/05* | (2006.01) |
| *A61B 1/06* | (2006.01) |
| *A61B 1/07* | (2006.01) |
| *A61B 1/12* | (2006.01) |

(52) U.S. Cl.
CPC .......... *A61B 1/00096* (2013.01); *A61B 1/009* (2022.02); *A61B 1/015* (2013.01); *A61B 1/018* (2013.01); *A61B 1/051* (2013.01); *A61B 1/0661* (2013.01); *A61B 1/07* (2013.01); *A61B 1/126* (2013.01); *A61B 1/00097* (2022.02); *A61B 1/05* (2013.01)

(58) Field of Classification Search
CPC ....... A61B 1/018; A61B 1/051; A61B 1/0661; A61B 1/07; A61B 1/126; A61B 1/05; A61B 1/00101; A61B 1/00128; A61B 1/00119; A61B 1/0008
See application file for complete search history.

(56) References Cited

U.S. PATENT DOCUMENTS

| | | | |
|---|---|---|---|
| 5,499,625 | A | 3/1996 | Frass et al. |
| 5,536,236 | A | 7/1996 | Yabe et al. |
| 5,562,602 | A | 10/1996 | Yabe et al. |
| 5,575,756 | A | 11/1996 | Karasawa et al. |
| 5,685,823 | A | 11/1997 | Ito et al. |
| 5,688,221 | A | 11/1997 | Yabe et al. |
| 5,725,476 | A | 3/1998 | Yasui et al. |
| 5,788,628 | A | 8/1998 | Matsuno et al. |
| 6,248,060 | B1 | 6/2001 | Buess et al. |
| 6,409,657 | B1 | 6/2002 | Kawano |
| 6,447,445 | B1 * | 9/2002 | Hirano ................. A61B 1/0011 600/129 |
| 6,569,089 | B1 | 5/2003 | Covington et al. |
| 7,630,148 | B1 | 12/2009 | Yang et al. |
| 8,485,966 | B2 | 7/2013 | Robertson |
| 10,245,402 | B2 | 4/2019 | Daher et al. |
| 10,321,804 | B2 | 6/2019 | Jacobsen et al. |
| 10,406,309 | B2 | 9/2019 | Daher |
| 11,291,352 | B2 | 4/2022 | Vilhelmsen et al. |
| 11,786,108 | B2 | 10/2023 | Sørensen et al. |
| 12,349,866 | B2 | 7/2025 | Sørensen et al. |
| 2005/0119527 | A1 * | 6/2005 | Banik ................ A61B 1/00066 600/117 |
| 2005/0154262 | A1 * | 7/2005 | Banik ................... A61B 1/128 600/179 |
| 2007/0249907 | A1 | 10/2007 | Boulais et al. |
| 2008/0188715 | A1 | 8/2008 | Fujimoto |
| 2008/0200764 | A1 | 8/2008 | Okada |
| 2009/0227998 | A1 | 9/2009 | Aljuri et al. |
| 2009/0247831 | A1 | 10/2009 | Miyamoto et al. |
| 2009/0253964 | A1 | 10/2009 | Miyamoto |
| 2012/0041534 | A1 | 2/2012 | Clerc et al. |
| 2012/0172664 | A1 | 7/2012 | Hayman et al. |
| 2012/0259173 | A1 | 10/2012 | Waldron et al. |
| 2012/0316395 | A1 | 12/2012 | Koga |
| 2014/0150782 | A1 | 6/2014 | Vazales et al. |
| 2015/0223671 | A1 * | 8/2015 | Sung .................. A61B 1/00128 600/110 |
| 2015/0257633 | A1 * | 9/2015 | Hassidov ........... A61B 1/00128 600/127 |
| 2015/0272430 | A1 | 10/2015 | Oishi et al. |
| 2016/0213229 | A1 * | 7/2016 | Kitano ............... A61B 1/00112 |
| 2017/0245734 | A1 | 8/2017 | Kaneko |
| 2018/0078120 | A1 | 3/2018 | Poll et al. |
| 2018/0160886 | A1 | 6/2018 | Govani et al. |
| 2019/0282070 | A1 | 9/2019 | Vilhelmsen et al. |
| 2019/0282077 | A1 | 9/2019 | Sørensen et al. |
| 2019/0313891 | A1 | 10/2019 | Oka |
| 2020/0305699 | A1 * | 10/2020 | Herriges .............. A61B 1/0684 |
| 2021/0145265 | A1 * | 5/2021 | Morishima ............ A61B 1/053 |
| 2021/0228064 | A1 | 7/2021 | Sørensen et al. |
| 2021/0247604 | A1 * | 8/2021 | Endo .................. G02B 23/2484 |
| 2021/0290041 | A1 | 9/2021 | Morita |
| 2022/0183541 | A1 * | 6/2022 | Sczaniecka ........ A61B 1/00096 |
| 2022/0409854 | A1 * | 12/2022 | Gao ........................ A61B 1/018 |
| 2023/0019357 | A1 * | 1/2023 | Mitsuhashi .......... A61B 1/0676 |
| 2023/0054149 | A1 | 2/2023 | Sørensen et al. |
| 2023/0165438 | A1 * | 6/2023 | Tang ................... A61B 1/0676 600/175 |
| 2023/0414072 | A1 | 12/2023 | Sørensen et al. |
| 2024/0172932 | A1 * | 5/2024 | Mayer ................. A61B 1/0008 |

FOREIGN PATENT DOCUMENTS

| | | | |
|---|---|---|---|
| EP | 0497347 | A2 | 8/1992 |
| EP | 0587177 | A1 | 3/1994 |
| EP | 1759625 | B1 | 10/2008 |
| EP | 2106739 | A2 | 10/2009 |
| EP | 3539449 | A1 | 9/2019 |
| JP | H08286127 | A | 11/1996 |
| JP | H11188004 | A | 7/1999 |
| JP | 5566344 | B2 | 8/2014 |
| WO | 1994022358 | A1 | 10/1994 |
| WO | 2010066790 | A1 | 6/2010 |

OTHER PUBLICATIONS

Search Report issued by the European Patent Office, dated Aug. 7, 2020, for related Application No. EP20153967.3; 8 pages.
International Search Report and Written Opinion of International Application No. PCT/EP2020/083527, dated Jan. 19, 2021.
International Search Report and Written Opinion of International Application No. PCT/EP2020/083525, dated Apr. 1, 2021.
Office Action dated Dec. 17, 2024 in U.S. Appl. No. 17/794,743.
Examination report issued in European Patent Application No. 20 811 351.4, dated Mar. 26, 2025, 3 pages.
Examination report issued in European Patent Application No. 20 812 031.1, dated Apr. 15, 2025, 4 pages.

* cited by examiner

TIP PART FOR FORMING A TIP OF A DISPOSABLE INSERTION ENDOSCOPE

CROSS-REFERENCE TO RELATED APPLICATIONS

This application is a National Stage entry filed under 35 U.S.C. § 371 of International Application No. PCT/EP2020/083527, filed Nov. 26, 2020, which claims priority from and the benefit of European Patent Application No. EP20153967.3, filed Jan. 28, 2020; the contents of the aforementioned applications are incorporated herein by reference in their entirety.

TECHNICAL FIELD

The present disclosure relates to insertable medical vision devices, such as, but not limited to, endotracheal tubes and endoscopes, in particular disposable insertion endoscopes, more specifically to a tip part of such a vision device, to an endoscope with such a tip part, and to a method of manufacture of such a tip part.

BACKGROUND ART

Vision devices, such as endoscopes, are well known for visually inspecting inaccessible places such as human body cavities. Typically, the endoscope comprises an elongated insertion tube with a handle at the proximal end, as seen from the operator, and visual inspection means, such as a built-in camera including a vision sensor, at a distal end of the elongated insertion tube. This definition of the terms distal and proximal, i.e. "proximal" being the end closest to the operator and "distal" being the end remote from the operator, as used herein for endoscopes in general, is adhered to in the present specification. Electrical wiring for the camera and other electronics, such as one or more LEDs accommodated in the tip part at the distal end, runs along the inside of the elongated insertion tube from the handle of the endoscope to the tip part. A working or suction channel may run along the inside of the insertion tube from the handle to the tip part, e.g. allowing liquid to be removed from the body cavity or allowing for insertion of surgical instruments or the like into the body cavity. The suction channel may be connected to a suction connector, typically positioned at a handle at the proximal end of the insertion tube.

To be able to manoeuvre the endoscope inside the body cavity, the distal end of the endoscope may comprise a bending section with increased flexibility, e.g. a number of articulated segments of which the tip part or an external housing thereof may form the distalmost segment. The manoeuvring of the endoscope inside the body is typically done by tensioning or slacking pull wires also running along the inside of the elongated insertion tube from the tip part through the remainder of articulated segments to a control mechanism of the handle.

As the name indicates, endoscopes are used for seeing inside things, such as lungs or other human body cavities of a patient. Modern endoscopes are therefore typically equipped with a light source and a camera or vision receptor including a vision or image sensor. Provided that sufficient light is present, it is possible for the operator to see where the endoscope is steered and to set the target of interest once the tip has been advanced thereto. This therefore normally requires illumination of the area in front of the distal tip of the endoscope, in particular the field of vision of the camera(s). The light source, such as a light emitting diode or an optical fiber, may provide illumination.

Additionally, when, as in the present disclosure, the insertion tube of the endoscope is intended to be inserted into a human body cavity, the insertion tube should furthermore be sealed in a watertight manner. This is particularly the case for a distal tip part accommodating a camera, LED(s), and/or other delicate electronics, prone to malfunction or destruction if exposed to humidity.

One known way of sealing the tip part of an endoscope is disclosed in WO2010/066790. In this document, a transparent monolithic housing is formed around the electronics and working channel by placing the electronics and the tube forming the working channel in a mold of transparent material, such as silicone. A transparent UV curable resin is then inserted from the bottom of the mold to avoid bubbles to form in the transparent resin. Because the resin rises slowly from the bottom, the air is slowly expelled from top of the mold, without any risk of air bubbles being trapped in the mold. The resin is then cured using UV irradiation through the transparent mold to form the monolithic housing.

DISCLOSURE OF INVENTION

A first aspect of this disclosure relates to a tip part for forming a tip of a disposable insertion endoscope, the tip part comprising:

an exterior housing having an open proximal end for connection to other parts of the endoscope, the housing further having a distal front wall and a circumferential housing wall, the circumferential housing wall extending a total housing length H in a proximal direction from the distal front wall to the proximal end of the housing, the distal front wall and the circumferential housing wall enclosing an interior spacing of the tip part;

a camera assembly able to provide an image from light received from an object to be investigated; and a tube insertion sleeve provided within the interior spacing and fixed in relation to the distal front wall, the tube insertion sleeve being formed by a circumferential tube sleeve wall that extends a total tube sleeve length S from the distal front wall of the housing to a proximal end of the tube insertion sleeve so that the tube insertion sleeve comprises an open proximal end;

wherein the distal front wall has a fluid opening which is aligned with a distal end of the tube insertion sleeve, a proximal surface of the distal front wall surrounding the fluid opening to provide a tube abutment surface;

whereby a tube can be inserted through the proximal end of the tube insertion sleeve until a distal end of the tube abuts the tube abutment surface, whereby the distal end of the tube is positioned to allow fluid flow through the tube to and through the fluid opening.

The abutment surface may circumscribe the fluid opening. The abutment surface may be annular. A width of the abutment surface may be an extent the abutment surface extends from the tube sleeve wall to the fluid opening. A width of the abutment surface may extend from an interior surface of the tube sleeve wall to the fluid opening. The width may extend radially from the interior surface of the tube sleeve wall to the fluid opening. the width may extend substantially perpendicularly to the length of the tube sleeve wall. A width of the abutment surface may be measured radially from an interior surface of the tube sleeve wall and to the fluid opening. The width of the abutment surface may be equal to or less than $\frac{1}{30}$, $\frac{1}{29}$, $\frac{1}{28}$, $\frac{1}{27}$, $\frac{1}{26}$, $\frac{1}{25}$, $\frac{1}{24}$, $\frac{1}{23}$, $\frac{1}{22}$, $\frac{1}{21}$, $\frac{1}{20}$, $\frac{1}{19}$, $\frac{1}{18}$, $\frac{1}{17}$, $\frac{1}{16}$, $\frac{1}{15}$, $\frac{1}{14}$, $\frac{1}{13}$, $\frac{1}{12}$, $\frac{1}{11}$, $\frac{1}{10}$, $\frac{1}{9}$, $\frac{1}{8}$, $\frac{1}{7}$, $\frac{1}{6}$, $\frac{1}{5}$, $\frac{1}{4}$, $\frac{1}{3}$, $\frac{1}{2}$, $\frac{2}{5}$, $\frac{3}{5}$, $\frac{2}{3}$, $\frac{4}{5}$, or $\frac{9}{10}$ of the total tube sleeve length S. The width of the abutment surface may be equal to or less than a thickness of an inserted tube. The width may be equal to or greater than a thickness of an inserted tube. The width of the abutment surface may be equal to or less than a thickness of the tube sleeve wall. The width of the abutment surface may be equal to or greater than a thickness of the tube sleeve wall. The width of the abutment surface may be equal to or less than 10, 9, 8, 7, 6, 5, 4, 3, 2, 1, or 0.5 times a thickness of the tube sleeve wall.

The tube insertion sleeve may be formed integrally and in one piece with the exterior housing.

The circumferential tube sleeve wall may be at least partly formed by the circumferential housing wall. Alternatively, the circumferential tube sleeve wall may be formed separately of the circumferential housing wall i.e. not integrally or in one piece with the circumferential housing wall.

The tip part may comprise at least two, three, four, five, six or more tube insertion sleeves provided in the interior spacing. Each tube insertion sleeve may be formed by a circumferential tube sleeve wall. At least two, potentially at least three, of the tube insertion sleeves may be at least partly formed by a common circumferential tube sleeve wall. The circumferential tube sleeve wall of at least one tube insertion sleeve may be at least partly formed by the circumferential housing wall and at least partly by a circumferential tube sleeve wall of an adjacent tube insertion sleeve. Each tube insertion sleeve may be at least partly formed by a circumferential tube sleeve wall of an adjacent circumferential tube sleeve wall. One or more circumferential tube sleeve walls may be formed separately of the circumferential housing wall i.e. not integrally or in one piece with the circumferential housing wall.

This may have the advantage of reducing the footprint and thereby the required space for each tube insertion sleeve whereby the cross-sectional extent and/or diameter of exterior housing may be reduced.

At least a part of two tube insertion sleeves extending side-by-side may include an open slot extending longitudinally between them.

The open slot may allow for the two tubes to be positioned close to, potentially abutting, each other along a longitudinal direction when the tubes are positioned in the tube insertion sleeves.

Potentially, parts of the fluid channels along a longitudinal direction may be coinciding and/or parts of circumferential walls may be removed from the cut-outs where the fluid channels intersect each other.

Accordingly, outlets from two tubes and/or open proximal ends of two tube insertion sleeves may be shaped like the number "8", especially if the tubes have a rounded or circular cross-section.

This embodiment may make it possible to minimize dimensions of the tube insertion sleeves and/or tubes since they are positioned very close to each other. This may, in turn, allow for a reduction of a total cross-sectional or radial extent of the tip part and/or the exterior housing.

This embodiment may also make it possible or at least easier to mold the tube insertion sleeves since there is a connection between them.

The tube, which may alternatively be denoted a pipe, may be a working channel tube, fluid supply tube, fluid suction tube, or the like.

A tube may be positioned in each tube insertion sleeve. Each tube may extend through the tip part, potentially to a respective fluid source. Each tube may be provided separately from or not in one piece with the exterior housing. The tubes may be for gas, a second of the tubes may be for liquid.

In the context of the present disclosure, a tube is any component which allows tight fluid flow through it and which has a length above zero.

Positioning of tubes in the tube insertion sleeves may occur subsequent to manufacture of the exterior housing including tube insertion sleeve and potentially the camera window and/or the camera insertion sleeve. The one or more tubes may be inserted into the tube insertion sleeves in a proximal to distal direction, potentially through a proximally positioned opening of the exterior housing.

An outer diameter or largest outer cross-section of an outer surface of each tube may correspond to the diameter or largest cross section of each corresponding tube insertion sleeve.

The one or more tubes may have a constant diameter along its/their length(s). The one or more tubes may be flexible and may comprise or consist of a plastic or polymer material, such as PET, PE, or PP. The one or more tubes may be tubular and may be cylindrical.

The tip part may comprise a nozzle. The nozzle may be positioned at or in the distal front wall. The nozzle may be integrally formed and in one piece with the distal front wall. The nozzle may generally be suitable for ejection of both gas and liquid. The nozzle outlet may generally be for ejection of both gas and liquid. The nozzle may be an outlet for one or more of the tube insertion sleeves and/or tubes.

The tip part, in particular the one or more tubes, may be connected to or be connectable to one or more fluid sources. The fluid provided from the fluid sources may be liquid and/or air or gas. The liquid may be water. The gas may be carbon dioxide. Ejection of liquid from or a liquid jet ejected or sprayed from the nozzle may be used for flushing with liquid and thereby cleaning at least part of the front surface of the camera window. Ejected gas may be used for cleaning remaining liquid on the camera window off after flushing with liquid. The ejected gas may also be used for expanding a body volume. The gas may also be used for accelerating or otherwise affecting the liquid flow and/or the liquid flushing process.

The tube insertion sleeve may be tubular. The tube insertion sleeve may be a cylindrical shell. The tube insertion sleeve may have a circular cross-section, potentially along an entire length of the tube insertion sleeve. The tube insertion sleeve may have circular end surfaces at its proximal end and/or distal end. The interior surface of the tube insertion sleeve may be complementary to an exterior surface of a tube to be inserted. The circumferential housing wall be annular.

The tip parts according to this disclosure may make it possible to reduce external dimensions of the tip parts and may reduce costs and time in manufacture.

The tip of the disposable insertion endoscope may be a distal tip of the disposable insertion endoscope.

The tip part may further comprise a bending section having a distal end segment, the distal end of the bending section and the proximal open end of the housing potentially being adjoined to each other.

The tip part may further comprise a camera window positioned in or forming part of the distal front wall.

The camera assembly may further comprise a vision sensor, a lens stack, and a printed circuit board (PCB).

In the context of the present disclosure, a sleeve is any component which allows insertion of another component into it.

The exterior housing may comprise a first material, which may be a first polymer material. The exterior housing may be an outer most wall of the tip part. The exterior housing may be cup-shaped, the cup being formed by the distal front wall and the circumferential wall. The exterior housing may fluid seal the interior spacing. The first material may be a fluid tight material.

The circumferential housing wall may have a cylindrical or circular-cylindrical outer and/or inner surface. The circumferential housing wall may comprise or be a circumferentially extending cylindrical wall.

The circumferential housing wall may extend in a direction distally-to-proximally. The distal front wall may extend in a transverse direction, the transverse direction being transverse to the distally-to-proximally direction.

The distal front wall may be positioned oppositely from the proximal end of the housing. The distal front wall may be at least partly coinciding with a distal end of the tip part.

Additionally or alternatively, the camera assembly may comprise a casing potentially in the form of a lens barrel, positioned between a first light source and a vision sensor of the camera assembly, the casing potentially including a light shield configured to substantially prevent light from passing through the casing. The light shield may be provided in the form of a light shielding layer provided on the casing. The light shielding layer may be provided by an adhesive, potentially hardened glue. The glue may be opaque, potentially black. The light shielding layer may be provided around the lens stack holder. The camera window may be a transparent part in or of the exterior housing enabling light to enter into the tip part to be received by the image sensor.

The camera window may comprise a second material, which may be a second polymer material, and which may be different from said first polymer material of the exterior housing. The second material may be a fluid tight material. The camera window and the exterior housing may be integrally molded in one piece by a multi-component molding process. A front surface of the camera window may be in the same plane as a front surface of the exterior housing.

The first polymer material may include or consist of one or several polymers and/or further materials. One or more of said polymers may be plastic or thermoplastic polymers. Said first polymer material and a potential second polymer material (see below) may be selected from thermoplastic materials, thermoset materials, and elastomers. The second material may comprise or consist of a transparent material and/or may include or consist of several polymers and/or further materials. Said first polymer material and/or said second polymer material may be fiber-reinforced. The first material may be opaque at least in a set condition. Said first polymer material may also be selected for other properties, such as good adhesion to sealant materials and adhesives. Thus, the set said first polymer material may have better adhesion properties to glue than the second polymer material.

A first window part and a second window part of the camera window may be molded as one single piece of a second polymer material.

The first material may be opaque. This may allow the introduction of shading parts inter alia reducing stray light and glare into the vision receptor.

The first material may have better adhesion properties to glue than the second material. This may allow the circumferential housing wall to adhere efficiently to a sealing glue for sealing the interior spacing, and for an exterior sleeve or an outer sheath of the insertion tube of the endoscope to be securely adhered to the exterior or the interior of the circumferential housing wall.

The second material may be a thermoplastic material. This may allow the exterior housing to be produced in an efficient manner, such as by injection molding.

The vision sensor may be a camera sensor of a camera which may form part of the camera assembly.

The term "integrally formed in one piece" as used herein may involve that two or more parts are integrally molded in one piece with each other, potentially in a multi-component molding process as disclosed herein.

The circumferential housing wall may be a side wall and/or may have a substantially cylindrical shape. The distal front wall and camera window may be integrally formed or molded in one piece. The distal front wall and the circumferential housing wall may form a liquid-tight (except for any potential inlets, outlets, and openings) barrier or border between an exterior of the tip part or the environment and the interior spacing of the tip part. The exterior housing may also accommodate at least part of a working channel for supplying fluid to a working channel opening in the distal front wall.

By integrally forming the circumferential housing wall and distal front wall, a sealed tip part may be provided. Additionally, assembly of the tip part may be made simpler as fewer parts are required. Similarly by integrally forming the circumferential tube sleeve wall and the distal front wall, a sealed tube sleeve may be provided.

Additionally or alternatively, the exterior housing may essentially consist of the same material as the window, such as a transparent material.

This may provide the advantage that the first and second materials can be selected according to the desired properties, for instance a transparent material may be selected for the window and an opaque material may be selected for the exterior housing.

In this context and applying generally to this disclosure, the term "comprises" includes "consists essentially of".

The multi-component molding process may be a two-component molding process.

Additionally or alternatively, the camera window and/or distal front wall may comprise one or more light guides positioned in front of the one or more light sources, potentially directly in front of the one or more light sources. A light guide may be positioned on each side of the camera assembly.

Additionally or alternatively, the one or more light guides may be of a transparent material, potentially the same material as the camera window. The one or more light guides may have a predetermined length between at least one first light reception end adapted for receiving light from a respective light source and at least one second light emission end adapted to emit light. The one or more light guides may form an integral part of the exterior housing and/or the camera window. By integrating the one or more light guides in the exterior housing and/or the camera window, it becomes possible to provide a sealed front end of the tip part and at the same time provide a well-defined exit viewing angle for the light from a respective light source.

The camera window may also extend to be positioned in front of the one or more light sources, or a window part may include the camera window and one or more light windows as described further below. Alternatively, a light window provided separately from the camera window may be provided for the one or more light sources, the separate light window being provided in front of the one or more light sources, potentially in a distal front surface of the tip part.

The exterior housing may comprise a first window part arranged in front of the vision sensor in the field of view thereof and a second window part arranged in front of one or more light sources.

The exterior housing may comprise a first polymer material and a second polymer material, the second polymer material being transparent.

The lens stack may comprise one or more lenses and may be arranged between the vision sensor and the camera window. The one or more lenses may be arranged, potentially in a lens stack, in front of the vision sensor, potentially so that an optical axis of the lens, potentially of the one or more lenses, align or coincide with an optical axis of the vision sensor. A front or distal lens may form the camera window. The plurality of lenses may be spaced apart by at least one spacer, potentially a plurality of spacers. The camera assembly may comprise a printed circuit board (PCB) having at least one electrical component for converting light received by the camera assembly to an image. The camera window may have different shapes, such as circular, half-moon shaped etc. The camera window may comprise a plurality of window parts. The window parts may abut each other. The window parts may be fixed to each other, potentially by gluing or welding. The camera window may form part of the exterior housing. The camera window may be integrally formed or molded in one piece with the exterior housing. The camera window may be formed by a lens, potentially a front lens of a lens stack, of the camera assembly in which case this lens may be positioned in an opening of the housing.

Additionally or alternatively, the camera window may be a distal front window, potentially allowing the vision sensor to receive image information from the distal end of the tip part. An exterior surface of the camera window may form part of a distal front wall of the exterior housing.

Additionally or alternatively, the camera window may be a side window, for instance when the endoscope is a duodenum endoscope. In this case, the distal front wall may be a side distal front wall positioned at a lateral side surface of the tip part. The side window may allow the vision sensor to receive image information from a side, potentially from a radial direction, of the tip part. The exterior surface of the window may be an exterior side surface. Accordingly, the distal front wall may be a side distal front wall instead of a distal front wall.

Additionally or alternatively, the camera window may comprise a front window and a side window. Accordingly, the distal front wall may be both a distal and a side distal front wall.

The camera window may comprise, potentially consist essentially of, a transparent material. A transparent material can transmit some image information and may potentially be defined as allowing at least 50% of visible light entering the window at the exterior surface to pass through the window. The transparent material may be a polymer, glass, plastic polymer, or any other suitable material, e.g. silicone, or a combination thereof.

The tip part may further comprise a window part positioned at or in the distal front wall, wherein the window part comprises the camera window, and the window part is formed of a second polymer material, the second polymer material being different from said first polymer material.

The second polymer material being different from said first polymer material may involve that a composition of the two polymer materials is different and/or that the first polymer material comprises at least one component not included in the second polymer material, or reversely. For example, the first polymer material may comprise a polymer not included in the second polymer material, and/or reversely, and/or the first polymer material may comprise a specific polymer in one amount and the second polymer material comprises the same specific polymer in a different amount. Various physical or chemical properties, such as melting point and/or adhesive properties may similarly be different in the two polymer materials.

Alternatively, the window part is formed of the same material as the exterior housing, i.e. of the said first polymer material, which may in this case be transparent and/or translucent.

The window part may form part of the exterior housing or may be provided separately from the exterior housing.

The exterior housing may have been or may be manufactured in a two-component molding process, whereby the window part or camera window can potentially be said to be integrally molded in one piece with the distal front wall and the circumferential wall.

The window part may be positioned in a cut-out of the distal end wall and/or may extend into a cut-out of the circumferential wall.

The window part may further include one or more, such as two, light windows for distribution of light from light sources positioned within the spacing of the exterior housing. The camera window and the light window(s) may be integrally formed in one piece with each other, the light window(s) potentially being integrally molded in one piece with the camera window.

The window part and/or the camera window may be transparent and/or translucent. The light window(s) may similarly be transparent and/or translucent and/or may allow light from an object to be investigated to pass through the light window(s) to illuminate the object to be investigated. The object to be investigated will typically be provided in front of or distal to the distal front wall, the camera window, and the light window(s).

The camera window may generally be positioned with a center line of the camera window coinciding with a center line of a distal front surface of the tip part or of the exterior housing. Two light windows may be positioned one on each side of the camera window, potentially with an equal distance to the center lines.

The one or more light guides may each be positioned behind or proximally from a light window. The window part may comprise the light guide(s). The light guide(s) may thus be formed of the second polymer material.

Alternatively, the light guide is provided separately from the window part and/or of the same material as the exterior housing, i.e. of the first polymer material, which may in this case be transparent.

The light guide(s) may form part of the exterior housing or may be provided separately from the exterior housing.

The exterior housing may have been or may be manufactured in a two-component molding process, whereby the window part including the light guide(s) can potentially be said to be integrally molded in one piece with the distal front wall, and the circumferential wall.

The light window may be a distal end of the light guide.

The light guide(s) may extend in a proximal direction into the interior spacing of the exterior housing.

The camera window and/or the light window(s) and/or the light guide(s) may be integrally formed in one piece with each other, these parts potentially being integrally molded in one piece. The light guide(s) may be transparent.

In this specification, the term "to accommodate" may additionally or alternatively be defined as "to house" or "to enclose" or "to surround". For instance, the exterior housing may enclose or surround the vision sensor and/or the one or more light sources.

In this specification, the terms "integrally" or "integrally provided" or "integrally comprising" or similar may be defined as the associated features forming an integral part of a whole; and/or are in one piece, potentially molded in one piece; and/or are substantially inseparable by hand.

In this specification, the term "proximal" may be defined as being closest to an operator of the endoscope, and the term "distal" as being remote from the operator. The term "proximal-distal" may be defined as extending between these two extremes, in the present case proximal-distal may extend along a center axis of the tip part extending between a proximal extremity of the proximal end of the tip part and a distal extremity of the distal end of the tip part.

In this specification, the distal end of the tip part should not be construed to only comprise the most distal extremity of the tip part, rather the term "distal end of the tip part" should be understood as a portion of the tip part being distally positioned, e.g. a remaining portion of the tip part relative to the proximal or back end and/or a portion of the tip part for not being connected to other parts of the endoscope and/or a distally located half of the tip part. In some embodiments, the window may be a side window positioned at the distal or front end of the tip part.

In this specification, the term "interior" may be defined as being positioned in an interior space of the tip part, and the term "exterior" may be defined as being positioned in an exterior space of the tip part or as not being positioned in an interior space of the tip part. The exterior housing may include an exterior surface that forms an outer surface of the exterior housing or the tip part.

In this specification, an endoscope may be defined as a device adapted for viewing body cavities and/or channels of a human and/or animal body. The endoscope may for instance be a conventional flexible or steerable endoscope or a rigid endoscope or an endotracheal tube potentially provided with a camera and light source for ensuring the correct position of the endotracheal tube, for instance a laryngoscope. The endoscope may be a duodenum endoscope or a urethroscope, or, in particular, a gastroscope or a colonoscope.

In a development of the previous embodiment, the tube insertion sleeve is fluid tight and/or fluid sealed from a surrounding portion of the interior spacing.

The tube insertion sleeve may be fluid tight and/or fluid sealed against the distal front wall.

In an embodiment, the circumferential tube sleeve wall is at least partly formed by or coinciding with the circumferential housing wall.

In an embodiment, the tube insertion sleeve is formed integrally and in one piece with the distal front wall and/or with the circumferential housing wall.

The tube insertion sleeve, the distal front wall, and the circumferential housing wall may all be formed integrally and in one piece with each other. If the tip part comprises more than one tube insertion sleeve, one, or more, or all of the tube insertion sleeves may be formed integrally and in one piece with the distal front wall and/or the circumferential housing wall.

The tip part may comprise a camera insertion sleeve according to any one of the above embodiments.

A camera insertion sleeve may be positioned at a top of the interior spacing. A tube insertion sleeve for a working channel and working channel tube may be positioned below the camera insertion sleeve. One or more tube insertion sleeves may be positioned in a lateral spacing next to the working channel tube. The camera insertion sleeve and tube insertion sleeve for the working channel tube may delimit a lateral spacing within the tip part. One or more tube insertion sleeves such as for fluid supply, rinsing fluid, and/or fluid extraction may be positioned in the lateral spacing.

The tube insertion sleeve may be at least partly formed by or coinciding with the camera insertion sleeve. The tube insertion sleeve may be integrally molded in one piece with the camera insertion sleeve.

The tip part may comprise at least two, three, four, five, or six such tube insertion sleeves. The tube insertion sleeves may be distributed in a cross-section of the exterior housing and/or next to each other in a radial direction of the distal front wall the tube insertion sleeves may be positioned above or below and/or laterally next to each other in the cross-section of the exterior housing. The tube insertion sleeves may be positioned such that they partly coincide with each other and/or the circumferential housing wall and/or the camera insertion sleeve. At least two, three, four, five, six, or more tube insertion sleeves may be at least partly formed by or coinciding with the camera insertion sleeve. At least two, three, four, five, six, or more tube insertion sleeves may be integrally molded in one piece with the camera insertion sleeve.

The tip part may further comprise a camera window positioned at least partly in front of the vision device, the camera window being positioned in or forming part of the distal front wall so that light received from the object can pass through the window to the vision device.

In an embodiment, the total sleeve length S is less than the total housing length H.

The total sleeve length S may be equal to or less than $9/10$, $8/10$, $7/10$, $6/10$, $5/10$, $4/10$, $3/10$, $2/10$, $1/10$ of the total housing length H. Alternatively, the total sleeve length S is greater than the total housing length.

In an embodiment, the tube abutment surface is positioned equal to or less than $3/10$ of the total housing length H from a distal end surface of the distal front wall in the distal-proximal direction.

The tube abutment surface may be positioned equal to or less than $2/10$ or $1/10$, $1/11$, $1/12$, $1/13$, $1/14$, $1/15$, $1/16$, $1/17$, $1/18$, $1/19$, or $1/20$ of the total housing length H from the distal end surface of the distal front wall. This may allow the tube to be positioned deeper in the tip part and reduce the material required by the tip part in proximal-distal direction which may allow the tip part to be made more compact in a longitudinal direction.

In an embodiment, a tube, such as a working channel tube, fluid supply tube, fluid suction tube, or the like is inserted in the tube insertion sleeve, a distal end of the tube abutting the tube abutment surface, whereby the distal end of the tube is positioned to allow fluid flow through the tube to and through the fluid opening.

In a development of the previous embodiment, the inserted tube is fluid sealed against the tube insertion sleeve by an adhesive and/or sealant.

This may provide a fluid sealed tube in the tip part which may improve the fluid tightness of the tip part and reduce the requirements for other fluid sealing of the tip part and/or electrical components in the tip part.

The adhesive and/or sealant may be provided at the proximal end of the tube sleeve wall between the inserted tube and the tube sleeve wall. The adhesive and/or sealant may be provided between an interior surface of the circumferential tube sleeve wall and an exterior surface of the inserted tube. The adhesive and/or sealant may be provided between an interior surface of the proximal end of the tube insertion sleeve and an exterior surface of the inserted tube. Adhesive and/or sealant may be provided between a distal end surface of the tube and the abutment surface.

In an embodiment, an adhesive and/or sealant is provided between the abutment surface and the inserted tube.

In an embodiment, an adhesive and/or sealant is provided between an interior surface of the circumferential tube sleeve wall and the inserted tube.

In an embodiment, the interior spacing is substantially filled with an adhesive and/or sealant. The interior spacing may be substantially filled with an adhesive and/or sealant up to an adhesive and/or sealant level. The adhesive and/or sealant level may substantially coincide with the proximal end of the exterior housing. This may improve electrical insulation, fluid tightness and/or stability of tip part.

In an embodiment, the tip part further comprises a second tube insertion sleeve and the circumferential sleeve wall of at least one of the tube insertion sleeves is at least partly formed by or coinciding with the circumferential housing wall and at least partly formed by or coinciding with the circumferential sleeve wall of the other tube insertion sleeve.

In an embodiment, the tip part comprises at least three tube insertion sleeves, and the circumferential tube sleeve wall of at least one of the tube insertion sleeves is at least partly formed by or coinciding with the circumferential tube sleeve walls of the two other tube insertion sleeves.

In a development of the previous embodiment, the circumferential tube sleeve wall of the at least one tube insertion sleeves is at least partly formed by or coinciding with the circumferential tube sleeve walls of the two other tube insertion sleeves and also at least partly formed by or coinciding with the circumferential housing wall.

The circumferential tube sleeve wall of at least two, three, four or more tube insertion sleeves may be at least partly formed by or coinciding with the circumferential tube sleeve walls of at least one, two, three, four or more other tube insertion sleeves and also at least partly formed by or coinciding with the circumferential housing wall. This may reduce the footprint required by the tube insertion sleeves by "sharing" parts of their respective circumferential sleeve walls with other tube insertion sleeves. Reducing the space required by the tube insertion sleeves may allow the diameter of the exterior housing to be reduced.

In an embodiment, the tip part further comprises a camera insertion sleeve according to any one of the preceding claims, wherein at least one tube insertion sleeve is at least partly formed by and/or coinciding with the circumferential camera sleeve wall.

A second aspect of the present disclosure relates to a method of manufacture of a tip part, the tip part being for forming a tip of a disposable insertion endoscope, the method comprising:

providing an exterior housing of the tip part having an open proximal end for connection to other parts of the endoscope, the housing further having a distal front wall and a circumferential housing wall, the circumferential housing wall extending a total housing length H in a proximal direction from the distal front wall to the proximal end of the housing, the distal front wall and the circumferential housing wall enclosing an interior spacing of the tip part;

providing a tube insertion sleeve of the tip part within the interior spacing and fixed in relation to the distal front wall, the tube insertion sleeve being formed by a circumferential tube sleeve wall that extends a total tube sleeve length S from the distal front wall of the housing to a proximal end of the tube insertion sleeve so that the tube insertion sleeve comprises an open proximal end;

providing a camera assembly able to provide an image from light received from an object to be investigated;

providing a tube of the tip part; and wherein the distal front wall has a fluid opening which is aligned with a distal end of the tube insertion sleeve, a proximal surface of the distal front wall surrounding the fluid opening to provide a tube abutment surface;

inserting the tube into the tube insertion sleeve through the proximal end of the tube insertion sleeve until a distal end of the tube abuts the tube abutment surface, whereby the distal end of the tube is positioned to allow fluid flow through the tube to and through the fluid opening.

In a development of the previous embodiment, the method further comprises the step of providing an adhesive and/or sealant between a distal end of the tube and the abutment surface.

In an embodiment, the method further comprises the step of providing an adhesive and/or sealant between an interior surface of the tube insertion sleeve and an exterior surface of the tube.

The methods according to this aspect of the present disclosure may be methods of manufacture of a tip part according to any one, or any combination, of any one of the embodiments of tip parts as disclosed herein. The methods according to this aspect of the present disclosure may additionally or alternatively comprise any of the further method steps as disclosed herein, including those disclosed in relation to the tip parts of the present disclosure.

Additionally or alternatively, an adhesive and/or sealant may be provided at a proximal end of the tube insertion sleeve. The adhesive and/or sealant may be provided between an interior surface of the proximal end of the circumferential tube sleeve wall and an exterior surface of the tube. In this way, the tube may be fluid sealed in the tube insertion sleeve.

This may provide a tip part that is easier to assemble. Furthermore, it may ensure correct positioning of the camera assembly within the tip part.

In an embodiment, the method further comprises the step of integrally molding the exterior housing in one piece so that the distal front wall and the circumferential wall are molded in one piece with each other and so that the distal front wall and the tube insertion sleeve are integrally molded in one piece with each other.

If the tip part comprises more than one tube insertion sleeve, each tube insertion sleeve may be integrally molded in one piece with the distal front wall.

In a development of the previous embodiment, the step of integrally molding the exterior housing in one piece further comprises that the circumferential housing wall and the tube insertion sleeve are integrally molded in one piece with each other.

If the tip part comprises more than one tube insertion sleeve, each tube insertion sleeve may be integrally molded in one piece with the circumferential housing wall.

The molding step may involve or consist of injection molding. Injection molding is typically efficient in terms of quick reproduction of identical items.

The first and/or second material may be selected from thermoplastic materials, thermoset materials, and elastomers. The second material may comprise or consist of a transparent material. The first material may be opaque at least in a set condition. The first material and said first polymer material may also be selected for other properties, such as good adhesion to sealant materials and adhesives. Thus, the set first material may have better adhesion properties to glue than the second material or the second polymer material.

The second material may be transparent and/or may include the camera window and potentially one or more light windows and/or may be provided as disclosed herein with respect to the description of the tip parts of this disclosure.

The method may be a method of manufacture of the tip part according to any one of the embodiments of tip parts as disclosed herein.

The methods according to this aspect of the present disclosure may further comprise the steps of, and/or a method of manufacture of the tip parts according to this disclosure may comprise:

providing a molding tool;

introducing a first melted material into the molding tool, wherein the first material may be said first polymer material on a melted form;

introducing at least one second melted material different from the first material into the molding tool, wherein the second material may be said second polymer material on a melted form;

allowing the second material to set and form a combined external housing with the first material; and removing the combined external housing from the mold- ing tool.

This may allow the provision of an integrated unit for the tip external housing having different areas with different desired properties; specifically, the second material may form the camera window and potentially one or more light windows.

The molding tool may comprise a first cavity, a second cavity, and one or more cores. If applying injection molding, this may be advantageous since the molded object may shrink during cooling and therefore may tend to stick to the core. The first material may be allowed to set or partly set before the second material is introduced. This may provide well-defined boundaries between the two materials in the final integrated unit. Moreover, it may allow the first mold to stick to the core for the introduction into the second cavity of the molding tool. The volume of the second material introduced in the mold may be smaller than a volume of the first material introduced into the mold. This may be of advantage if the second material is more brittle than the first material because having a smaller volume thereof will make it less prone to stick to the mold due to shrinking, thereby making it easier to extract from the mold. Accordingly, the second material may also be injected at higher pressure than the first material because a high pressure used for the first material will make it more prone to sticking to the mold and/or core(s), in turn making removal more difficult. Accordingly, the introduction of the first and/or the second material may form part of an injection molding process.

The second material may comprise or consist of a trans- parent material. Injecting the transparent material as the second material may be advantageous because transparent materials, which are preferred for their optical properties, may then be introduced under higher pressure than the first material. This, in turn, may reduce shrinking and may provide improved control of the optical properties of the manufactured tip part. The second material, which may be more brittle, may generally constitute only a minor part of the total material of the exterior housing. This may make it is easier to remove the exterior housing from the mold. The first material may accordingly be opaque at least in its set form. The first material and said first polymer material may alternatively or additionally be selected for other properties, such as good adhesion to sealant materials and adhesives. Thus, the set first material may have better adhesion prop- erties to glue than the second material or the second polymer material. The first cavity and the second cavity may have generally cylindrical shapes. This may result in a generally cylindrical exterior housing which, in turn, may be suitable for endoscopes made with the tip part according to the present disclosure.

In an embodiment, the method further comprises the step of integrally molding the exterior housing, the camera window, the camera insertion sleeve and potentially one or more tube insertion sleeves in one piece with each other in a multi-component molding process, in which molding process the exterior housing and the camera window are manufactured from two different materials.

Alternatively, in such a multi-component molding pro- cess, the window part is formed of the same material as the exterior housing, i.e. of the said first polymer material, which may in this case be transparent and/or translucent. In this case, either the exterior housing or the camera window may be manufactured with master batch, the other without.

A third aspect of the present disclosure relate to an endoscope comprising a tip part according to any one of the embodiments of the first aspect and/or comprising a tip part manufactured according to any one of the embodiments of the second aspect.

The endoscope may be a disposable insertion endoscope. The endoscope may include one or more features as described herein in the above, including the features described in the above introduction to this description, and in connection with the description of the methods and tip parts according to the present disclosure.

The endoscope may comprise an elongated insertion tube with a handle at the proximal end. The tip part may be positioned at the distal end of the elongated insertion tube. The tip part may further comprise a bending section posi- tioned between the tip part and the elongated insertion tube. The bending section may be configured to be articulated to maneuver the endoscope inside a body cavity.

A fourth aspect of the present disclosure relates to a system comprising:

an endoscope comprising a tip part according to any one of the embodiments of the first aspect and/or compris- ing a tip part manufactured according to any one of the embodiments of the second aspect: and a display for displaying an image provided by the camera assembly.

A person skilled in the art will appreciate that any one or more of the above aspects of this disclosure and embodi- ments thereof may be combined with any one or more of the other aspects and embodiments thereof.

BRIEF DESCRIPTION OF DRAWINGS

In the following, non-limiting exemplary embodiments will be described in greater detail with reference to the drawings, in which.

DETAILED DESCRIPTION

Figure 1:
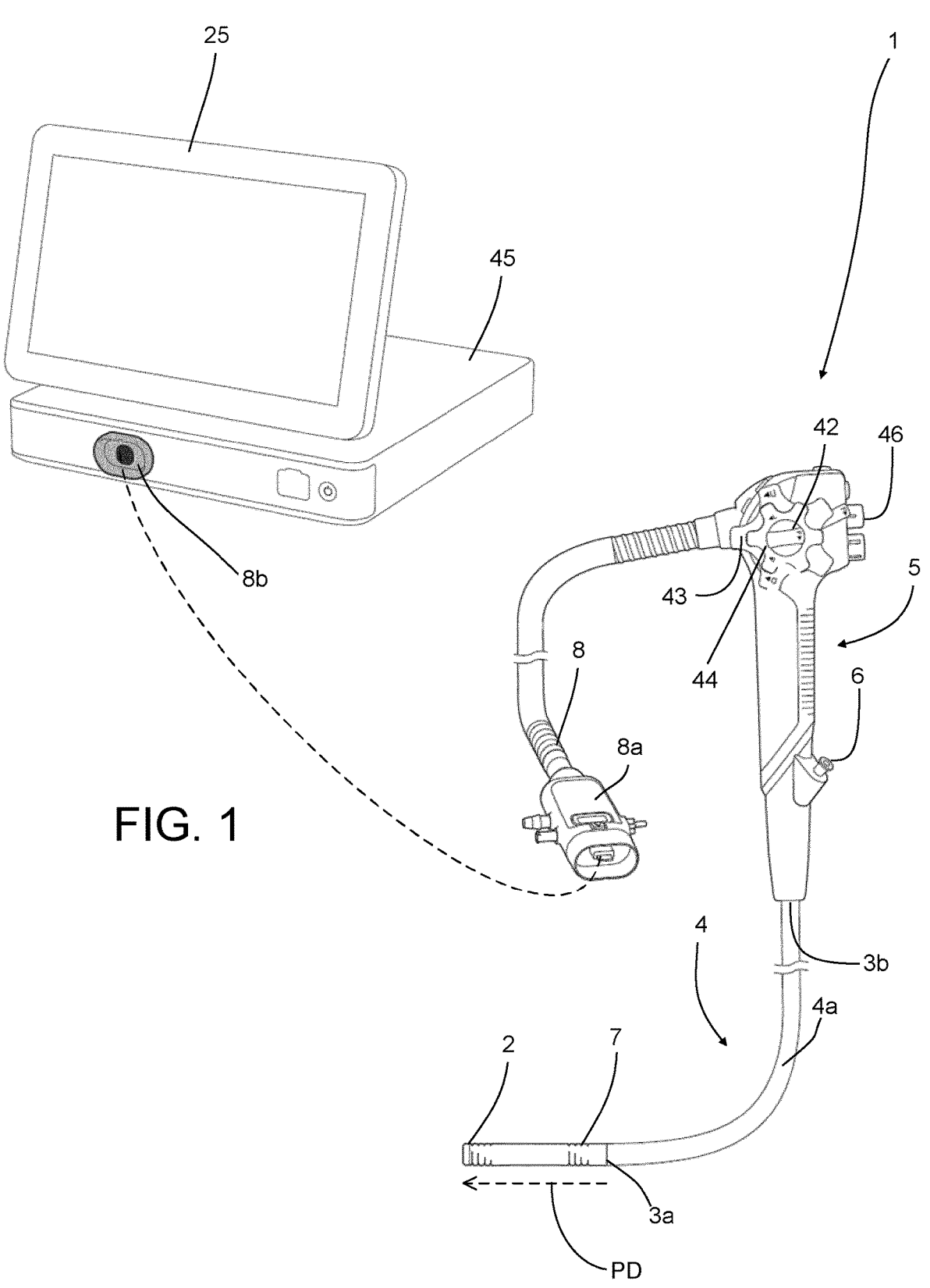
FIG. 1 shows an embodiment of a system comprising a disposable insertion endoscope and a display according to the present disclosure.
Figure 2:
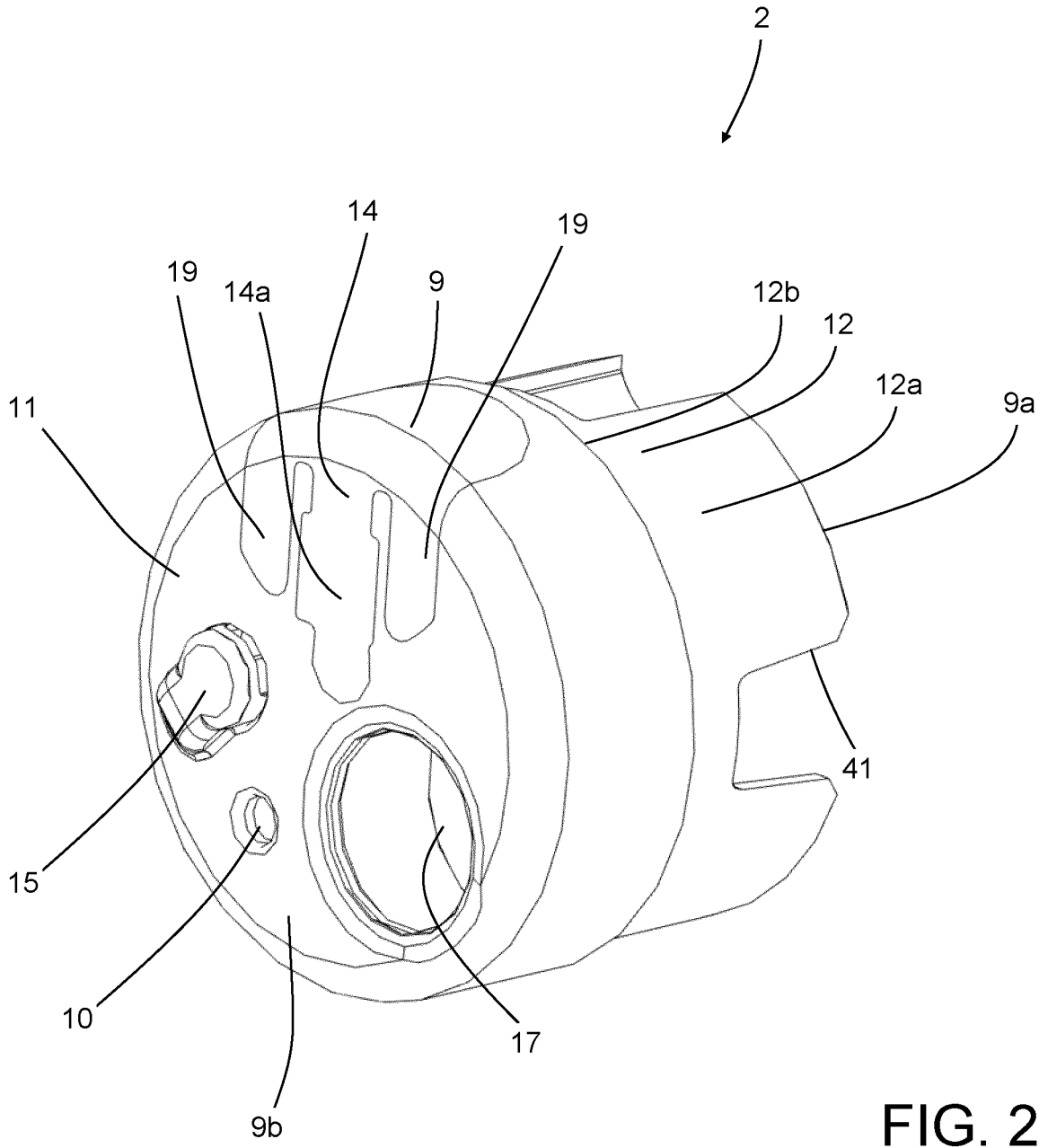
FIG. 2 shows a front perspective view of a tip part of the endoscope of FIG. 1.

FIG. 1 shows an endoscope 1 according to an embodiment of the endoscopes of the present disclosure, in particular a gastroscope. In other embodiments, the endoscope is another type of endoscope, such as a bronchoscope, urethroscope, a colonoscope, a rhinolaryngoscope, a cystoscope, or a duodenoscope. The endoscope 1 is or can be connected to a display 26 shown in FIG. 1. The endoscope 1 is disposable and single-use, i.e. not intended to be cleaned and reused. The endoscope 1 comprises an elongated insertion tube 4. At a proximal end 3*b* of the insertion tube 4, an operating handle 5 is arranged. The operating handle 5 has a control lever 42, which is known per se and comprises two control knobs 43, 44, respectively, for maneuvering a tip part assembly including the tip part 2 and bending section 7 attached at a distal end of the insertion tube 4 by means of one or more not shown steering wires. In a known operation of the control lever 42, each knob 43, 44 is operated by one or more fingers of an operator to control a bending operation of the tip of the endoscope 1, through the bending section 7 which allows bending in two dimensions, each direction corresponding to the operation of one of the two knobs 43, 44. The control lever 42 can comprise a known locking or arresting mechanism, upon activation of which a selected bending configuration of the tip can be achieved in a known manner. Other known types of control systems could alternatively be implemented in the endoscopes of the present disclosure.

The tip part 2 is positioned at a distal end 3*a* of an elongated insertion tube 4 of the endoscope 1. In the shown embodiment, the bending section 7 is positioned between the tip part 2 and the insertion tube 4. The bending section 7 is configured to be articulated to maneuver the endoscope 1 inside a body cavity. The handle 5 is connected to a fluid hose 8 for supplying fluid to the tip part 2. The fluid hose 8 is to be connected, via plug 8*a*, to the plug receiver 8*b* of the combined image processing and fluid supply unit 45. Flow of fluid through the endoscope 1 can be controlled via control dials 46. The plug 8*a* also comprises electric wires for connecting the display 26 to the endoscope 1 to display and view an image provided by the camera assembly 27. A working channel inlet 6 is also provided on the handle 5.

FIGS. 2 to 5 show different views of the tip part 2. The tip part 2 includes an exterior housing 9 having an open proximal end 9*a* for connection to the more proximally positioned parts of the endoscope 1. The housing 9 further comprises a distal front wall 11, wherein a cylindrically shaped circumferential housing wall 12 of the housing 9 extends from a distal front end 9*b* of the housing 9 to the proximal end 9*a* of the housing 9. The circumferential housing wall 12 and the front wall 11 enclose an interior spacing 24 accommodating camera assembly 27 with a vision sensor 29 able to provide an image from light received from an object to be investigated. The front wall 11 is positioned oppositely from the proximal end 9*a* of the housing 9 and coincides with the distal end of the tip part 2. The circumferential housing wall 12 extends from the front wall 11 to the proximal end 9*a* of the housing 9.

The housing 9 further comprises a nozzle 15 provided at the distal end of the tip part 2 for flushing an exterior surface 14*a* of a camera window 14 with a liquid transferred to the nozzle 15 from the fluid source.

The front wall 11 and the circumferential housing wall 12 are integrally molded from a first polymer material and are in one piece with each other. The front wall 11, the nozzle 15, are similarly integrally molded from said first polymer material and are in one piece with each other. The front wall 11, the circumferential housing wall 12, and the nozzle 15 are integrally molded from a first polymer material and are in one piece with each other.

The exterior housing 9 is generally cup-shaped, the cup being formed by the front wall 11 and the circumferential housing wall 12.

The nozzle 15 is a liquid nozzle for ejection of liquid and also functions as a gas nozzle for ejection of gas.

Said first polymer material is opaque and consists of, or comprises or consists essentially of, a thermoplastic polymer. The camera window 14 is manufactured of a second polymer material which is transparent and similarly comprises a thermoplastic polymer.

The circumferential housing wall 12 is a circumferentially extending cylindrical wall which has a generally cylindrical outer surface 12*a* and includes a step 12*b* for positioning of a flexible external sleeve or outer sheath 4*a* which extends from the proximal end 3*b* to the step 12*b*, surrounding the insertion tube 4 and part of the tip part 2.

The front wall 11 of the housing 9 includes liquid and gas fluid openings 16*a*, 16*b* which is an opening in the front wall 11 for introducing liquid into the nozzle 15. The front wall 11 of the housing 9 also includes a working channel opening 17 and a rinsing fluid opening 10 for ejecting a water jet.

The tip part 2 or the endoscope 1 further comprises the bending section 7 which has a distal end segment, a distal end of the bending section 7 and the proximal open end 9*a* of the housing 9 being adjoined to each other by means of articulated sections, a proximal end section of the latter being adjoined to the tip part 2.

A camera window 14 is positioned in front of the vision sensor 29, the camera window 14 being positioned in the front wall 11 so that light received from the object can pass through the window 14 to the vision sensor 29 as is conventional in endoscopes.

The camera window 14 comprises a second polymer material, which is different from said first polymer material of the exterior housing 9. The camera window 14 and the exterior housing 9 are integrally molded in one piece by a multi-component molding process according to the methods of the second aspect of this disclosure. The exterior front surface 14*a* of the camera window 14 is located in the same plane as a front surface of the exterior housing 9, specifically of the front wall 11.

A distal front surface of the camera window 14 extends along the distal end surface of the tip part 2 in a plane common with a distal end surface of the front wall 11. The camera window 14 is also positioned so that its distal end surface extends from the distal surface of the camera window 14 into the circumferential housing wall 12 to have a side surface completing the cylindrical external surface of the circumferential housing wall 12. The camera window 14 comprises several window parts, all being in one piece with each other. The camera window 14 can potentially be said to form part of the exterior housing 9, a distal front surface of the camera window 14 forming part of a distal surface of the housing 9 or the front wall 11 thereof, and the side surface of the camera window 14 forming part of the circumferential side surface of the housing 9 or the circumferential housing wall 12.

The camera window 14 is a distal front window allowing the camera assembly 27 to receive image information from the distal end of the tip part 2, i.e. from an object, such as a body cavity or body part, positioned in front of the camera window 14. The exterior distal front surface of the camera window 14 can be considered as forming part of the distal front wall 12 of the exterior housing 14.

The entire camera window 14 is integrally molded in one piece with the exterior housing 9 in a two-component molding process, see further below. The camera window 14 consists of a second, transparent plastic polymer material, this second polymer material being different from said first polymer material of which the exterior housing including the circumferential housing wall 12 and the front wall 11 are molded.

As mentioned, the exterior housing 9 including the circumferential housing wall 12, the front wall 11 and the camera window 14 have been manufactured in a two-component molding process, whereby the camera window is integrally molded in one piece with the front wall 11, the circumferential housing wall 12, and the nozzle 15.

The camera window 14 includes a camera window part 18 positioned in front of the vision sensor 29 positioned within the tip part 2 and two light window parts 19 extending to be positioned in front of two light sources 30, specifically LEDs, which are positioned within the tip part 2. Alternatively, the camera window part 18 can be considered "the camera window", and the light window parts can be considered "light windows". The light window parts 19 are for distribution of light from the LEDs positioned within the spacing of the exterior housing 9. The camera window part 18 and the light window parts 19 are integrally molded in one piece with each other.

Figure 3:
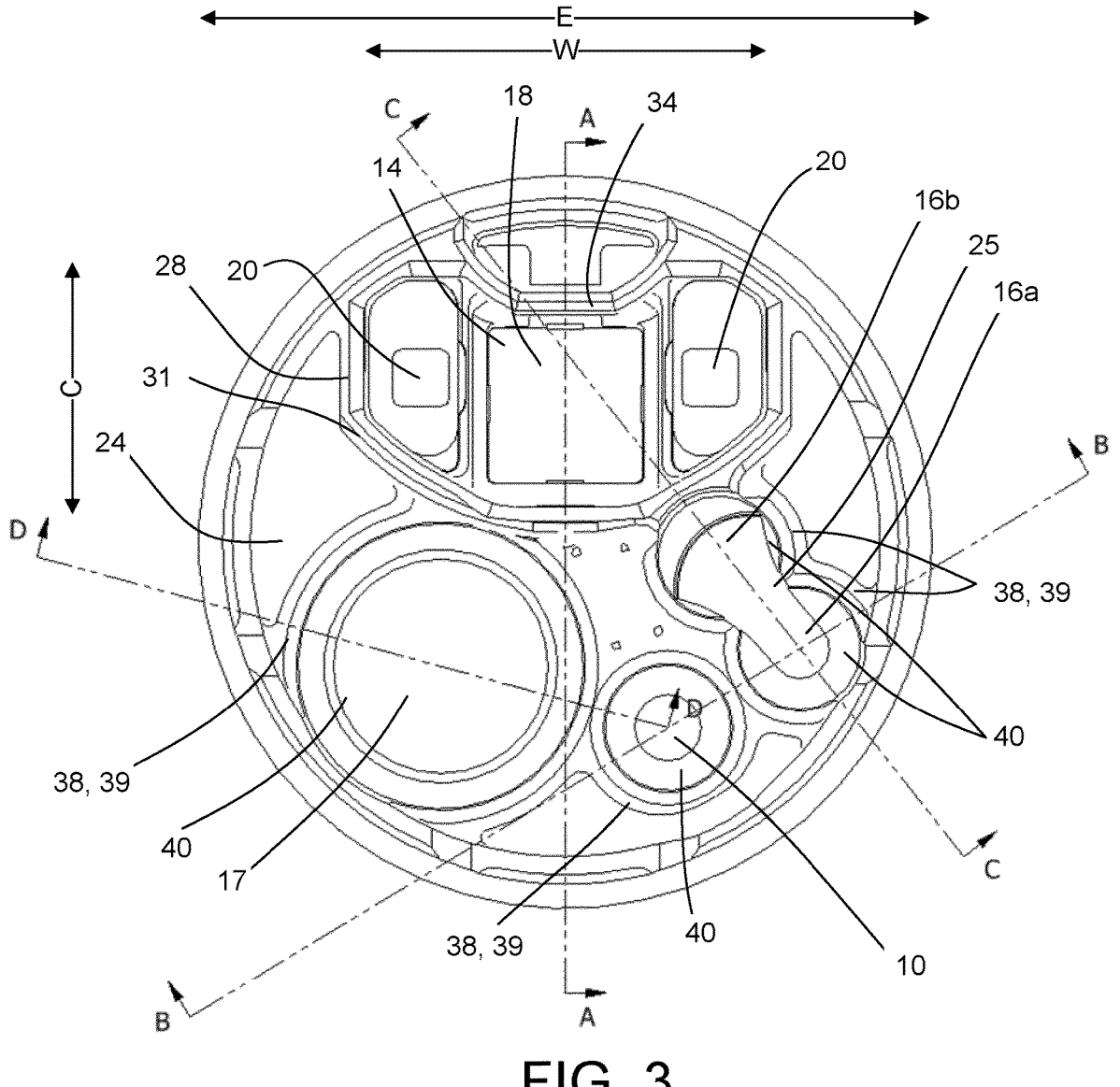
FIG. 3 shows a rear view of the tip part of FIG. 2.

As shown in FIG. 3, the camera window part 18 is positioned with a center line of the camera window coinciding with a center line A-A of the distal front surface or the front wall 11 of the tip part 2 and of the exterior housing 9. The two light window parts 19 are positioned one on each side of the camera window part 18, symmetrically with respect to and with an equal distance to the center line A-A.

Alternatively, in a not shown embodiment, the camera window 14 is instead a side window, for instance if the endoscope were a duodenum endoscope. In this case, the front wall 11 can be a side front wall positioned at a lateral side surface of the tip part 2. Such a side window may allow the camera assembly to receive image information from a side, potentially from a radial direction, of the tip part 2. Accordingly, the front wall 11 may be a side front wall instead of a distal front wall as shown in the embodiment of the drawings.

In the embodiment shown in the figures, the light window parts 19 of the camera window 14 each includes a light guide 20, which each extends proximally from the distal font surface of the camera window 14 towards each of the two LEDs. One LED is positioned at a proximal end of each light guide 20. The camera window part 18 and the light windows 19 including the light guides 20 are integrally molded in one piece with each other from the said second polymer material. The light guides 20 are similarly transparent and convey and control light from the LEDs as is known in the art.

The nozzle 15 is formed integrally with the front wall 11 as a single piece of the one or the first polymer material from which the exterior housing 9 including the front wall 11 and the circumferential housing wall 12 are molded. This first polymer material is opaque, which allows the introduction of not shown shading parts reducing stray light and glare into the vision sensor.

The first polymer material has better adhesion properties to glue than the second polymer material. This allows the circumferential housing wall 12 to adhere efficiently to a sealing glue sealing the interior spacing, and for the outer sheath 4a covering the insertion tube 4 to be securely adhered to the part of exterior surface of the circumferential housing wall 12 extending proximally from the step 12b.

The first and second polymer materials are thermoplastic polymer materials which allows the exterior housing 9 including the camera window 14 to be produced by injection molding in said two-component molding process.

Hereby, the front wall 11, the circumferential housing wall 12 and the camera window form a liquid-tight (except for intended outlets and openings) barrier or border between an exterior of the tip part 2 or the environment and the interior spacing 24 of the tip part 2.

By integrally forming the circumferential housing wall and camera window, a sealed tip part 2 is provided. Additionally, assembly of the tip part 2 is made simpler since fewer parts are required.

The distal, exterior front surface of the tip part 2 or front surface 11 is substantially planar.

The circumferential housing wall 12 extends from this front surface along lateral sides of the components positioned within the interior spacing. The circumferential housing wall 12 thus extends in the direction PD shown in FIG. 1. The front wall 11 extends in a direction transverse to the direction PD.

The tip part 2 further comprises tube insertion sleeves 38 provided within the interior spacing 24 and fixed in relation to the distal front wall 11. The tube insertion sleeves 38 being formed by circumferential tube sleeve walls 39 that extend a total tube sleeve length S from the distal front wall 11 of the housing 9 to a proximal end of the tube insertion sleeves 39 so that the tube insertion sleeves 38 comprises open proximal ends. The distal front wall 11 having fluid openings 10, 16a, 16b, 17 which are aligned with a distal end of the tube insertion sleeves 38, a proximal surface of the distal front wall 11 surrounding the fluid openings 10, 16a, 16b, 17 to provide tube abutment surface 40.

A tube 13, 21, 22, 23 can be inserted through the proximal end of the tube insertion sleeve 38 until a distal end of the tube abuts the tube abutment surface 40, whereby the distal end of the tube is positioned to allow fluid flow through the tube to and through the fluid opening 10, 16a, 16b, 17, see particularly FIGS. 6-11.

The abutment surface 40 circumscribes the fluid openings 10, 16a, 16b, 17. The abutment surface 40 is annular. The width A of the abutment surface 40 is an extent the abutment surface 40 extends from the tube sleeve wall 39 to the fluid opening 10, 16a, 16b, 17. The width A extends substantially perpendicularly to the length S of the tube sleeve wall 39. The width A of the abutment surfaces 40 less than ⅓ the total tube sleeve length S. The width of the abutment surface may be equal to or less than a thickness of an inserted tube. The width A of some of the abutments surfaces 40 is greater than the thickness of the inserted tube 21, 22, 23 and for some is less than the thickness of the inserted tube 13. The width of the abutment surfaces 40 is greater than the thickness of the tube sleeve walls 39. The tube insertion sleeves 38 are formed integrally and in one piece with the exterior housing 9. Some of the circumferential tube sleeve walls 39 are partly formed by the circumferential housing wall 12.

The tip part in the shown embodiment comprises four tube insertion sleeves 38 provided in the interior spacing 24. Each tube insertion sleeve 38 is formed by a circumferential tube sleeve wall 39. The tube insertion sleeves 38 are partly formed by a common circumferential tube sleeve wall 39. The circumferential tube sleeve wall 39 of two of the tube insertion sleeves 38 are partly formed by the circumferential housing wall 12 and partly by a circumferential tube sleeve wall 39 of an adjacent tube insertion sleeve 38.

Two tube insertion sleeves 38 extend side-by-side and include an open slot 25 extending longitudinally between them. The open slot 25 allow for the two tubes 21, 22 to be positioned close to each other along a longitudinal direction when the tubes 21, 22 are positioned in the tube insertion sleeves 38. Parts of the tube insertion sleeves 38 along a longitudinal direction are coinciding. Parts of two of circumferential tube sleeve walls 38 are removed from cut-outs where the tube insertion sleeves 38 intersect each other. Accordingly, outlets from two tubes 21, 22 and open proximal ends of two tube insertion sleeves 38 are shaped like the number "8".

A tube 13, 21, 22, 23 is positioned in each tube insertion sleeve 38. Each tube 13, 21, 22, 23 extends through the tip part 2. Each tube 13, 21, 22, 23 is provided separately from and not in one piece with the exterior housing 9. Liquid tube 21 is for liquid, gas tube 22 is for gas, and rinsing fluid tube 23 is for rinsing fluid. Working channel tube 13 is for the working channel and may be used for fluid supply or extraction, or for insertion of tools or the like.

Positioning of the tubes 13, 21, 22, 23 in the tube insertion sleeves 38 occurs subsequent to manufacture of the exterior housing 9 including tube insertion sleeves 38 and the camera window 14 and the camera insertion sleeve 28. The tubes 13, 21, 22, 23 are inserted into the tube insertion sleeves 38 in a proximal to distal direction, through the proximally positioned opening of the exterior housing 9.

An outer diameter or largest outer cross-section of the outer surface of each tube 13, 21, 22, 23 corresponds to the diameter or largest cross section of each corresponding tube insertion sleeve 38.

The tubes 13, 21, 22, 23 have a constant diameter along their lengths. The tubes 13, 21, 22, 23 are flexible and comprise a plastic or polymer material, such as PET, PE, or PP. The tubes 13, 21, 22, 23 are tubular and cylindrical.

The tip part 2, in particular the tubes 13, 21, 22, 23, are connectable to one or more fluid sources not shown. The fluid provided from the fluid sources may be liquid and/or air or gas. The liquid may be water. The gas may be carbon dioxide. Ejection of liquid from or a liquid jet ejected or sprayed from the nozzle 15 is used for flushing with liquid and thereby cleaning at least part of the front surface of the camera window 14. Ejected gas is used for cleaning remaining liquid on the camera window 14 off after flushing with liquid. The ejected gas is also be used for expanding a body volume. The gas is also used for accelerating or otherwise affecting the liquid flow and the liquid flushing process.

The tube insertion sleeves 38 are tubular having a cylindrical shell. The tube insertion sleeves 38 have a circular cross-section. Some of the tube insertion sleeves 38 have circular end surfaces at their proximal end and distal end. The interior surface of the tube insertion sleeves 38 are complementary to an exterior surface of the tube 13, 21, 22, 23 to be inserted.

The tube insertion sleeves 38 are fluid tight and fluid sealed from the surrounding portion of the interior spacing 24.

The tube insertion sleeves 38 are fluid tight and fluid sealed against the distal front wall 11.

The tube insertion sleeves 38 are formed integrally and in one piece with the distal front wall 11 and the circumferential housing wall 12.

The camera insertion sleeve 28 is positioned at a top of the interior spacing 24. The tube insertion sleeve 38 for the working channel and working channel tube 13 is positioned below the camera insertion sleeve 28. Three tube insertion sleeves are positioned in the lateral spacing next to the working channel tube 13. The camera insertion sleeve 28 and tube insertion sleeve 38 for the working channel tube 13 delimit a lateral spacing within the tip part 2. Tube insertion sleeves 38 for fluid supply and rinsing fluid are positioned in the lateral spacing.

Two of the tube insertion sleeves 38 are partly formed by and coinciding with the camera insertion sleeve 28. The tube insertion sleeves 38 are integrally molded in one piece with the camera insertion sleeve 28.

The tube insertion sleeves 38 are distributed in a cross-section of the exterior housing 9 and next to each other in a radial direction of the distal front wall 11. The tube insertion sleeves 38 are positioned above, below and laterally next to each other in the cross-section of the exterior housing 9. The tube insertion sleeves 38 are positioned such that they partly coincide with each other and some of the tube insertion sleeves partly coincide with the circumferential housing wall 12 and the camera insertion sleeve 28. Two, of the tube insertion sleeves 38 are partly formed by and coinciding with the camera insertion sleeve 28.

The total sleeve lengths S are less than the total housing length H.

The total sleeve lengths S are less than $\frac{3}{10}$ of the total housing length H.

The tube abutment surfaces 40 are less than $\frac{3}{10}$ of the total housing length H from the distal end surface of the distal front wall 11 in the distal-proximal direction.

A tube 13, 21, 22, 23 is inserted in each of the tube insertion sleeves a distal end of the tube abutting the tube abutment surface 40, whereby the distal end of the tube is positioned to allow fluid flow through the tube to and through the fluid opening as seen in FIGS. 7, 9, 11, and 12. The inserted tubes 13, 21, 22, 23 are fluid sealed against the tube insertion sleeves 38 by an adhesive and sealant not shown. The adhesive and sealant is provided at the proximal end of the tube sleeve walls 39 between the inserted tube 13, 21, 22, 23 and the tube sleeve wall 39. The adhesive and sealant is provided between an interior surface of the circumferential tube sleeve wall 39 and an exterior surface of the inserted tube 13, 21, 22, 23. An adhesive and sealant is also provided between the respective abutment surface 40 and the inserted tube 13, 21, 22, 23.

Figure 4:
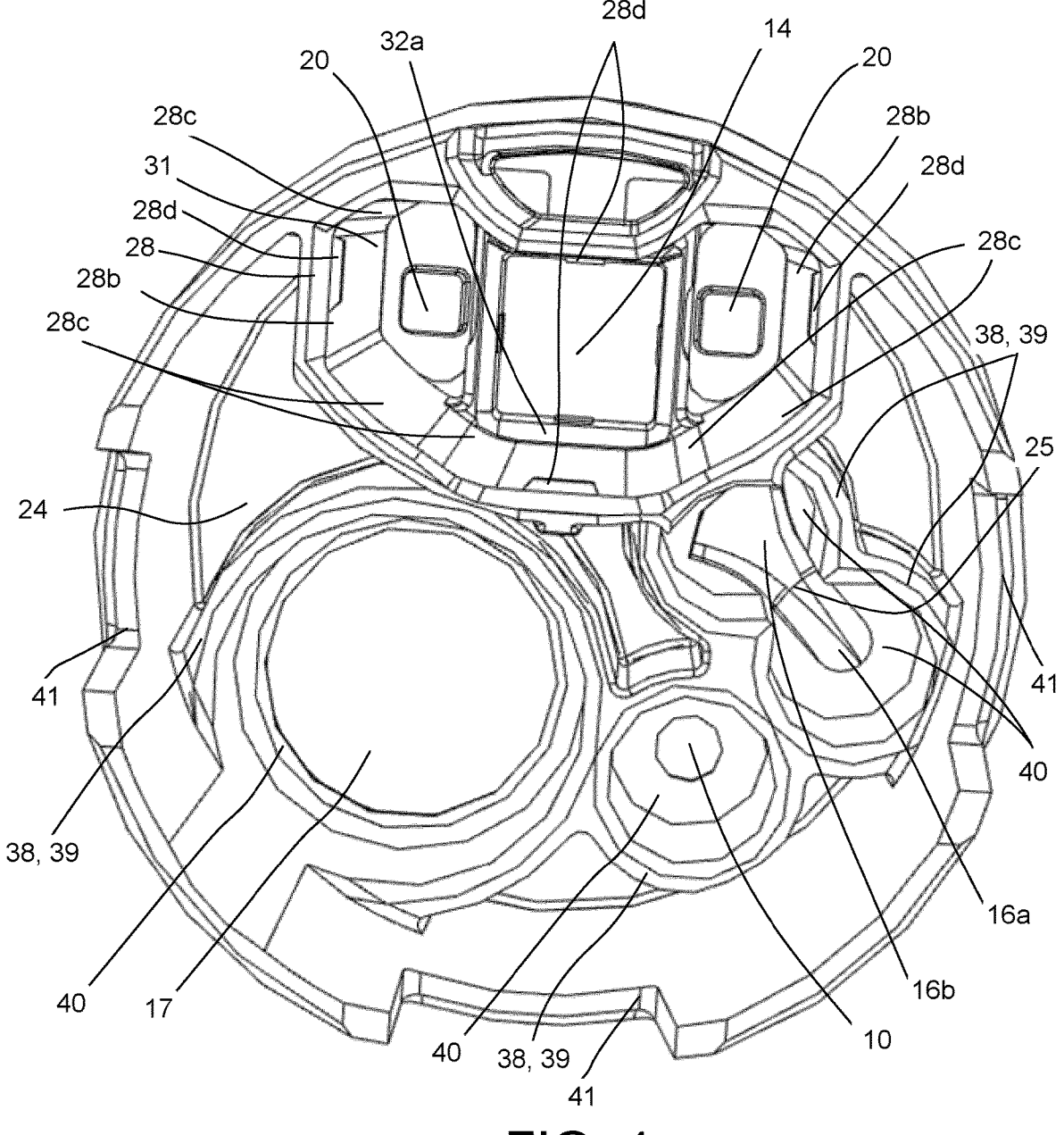
FIG. 4 shows a perspective rear view of the tip part of FIG. 2.
Figure 5:
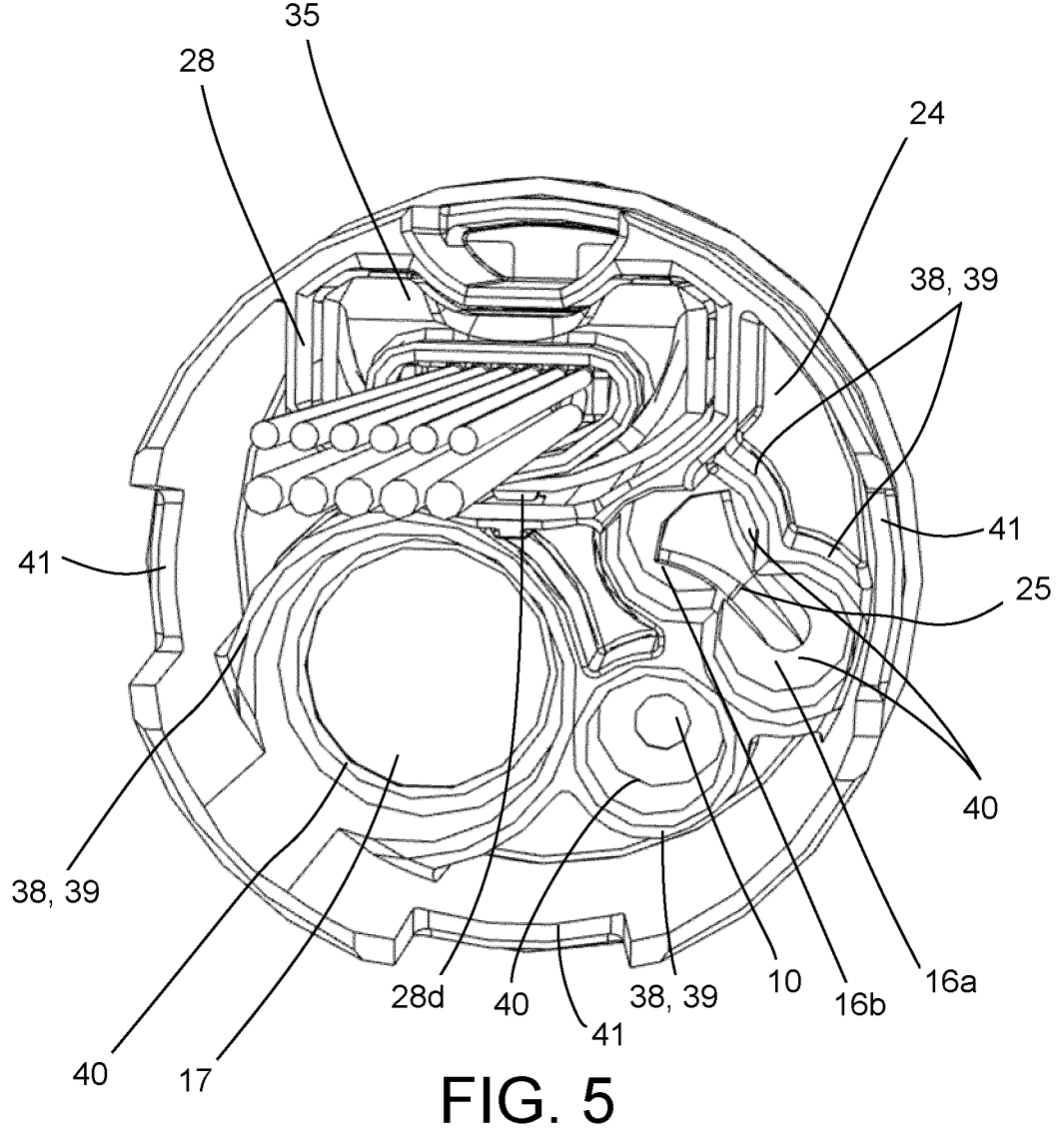
FIG. 5 shows a perspective rear view of the tip part of FIG. 2 with inserted camera assembly.
Figures 6, 7:
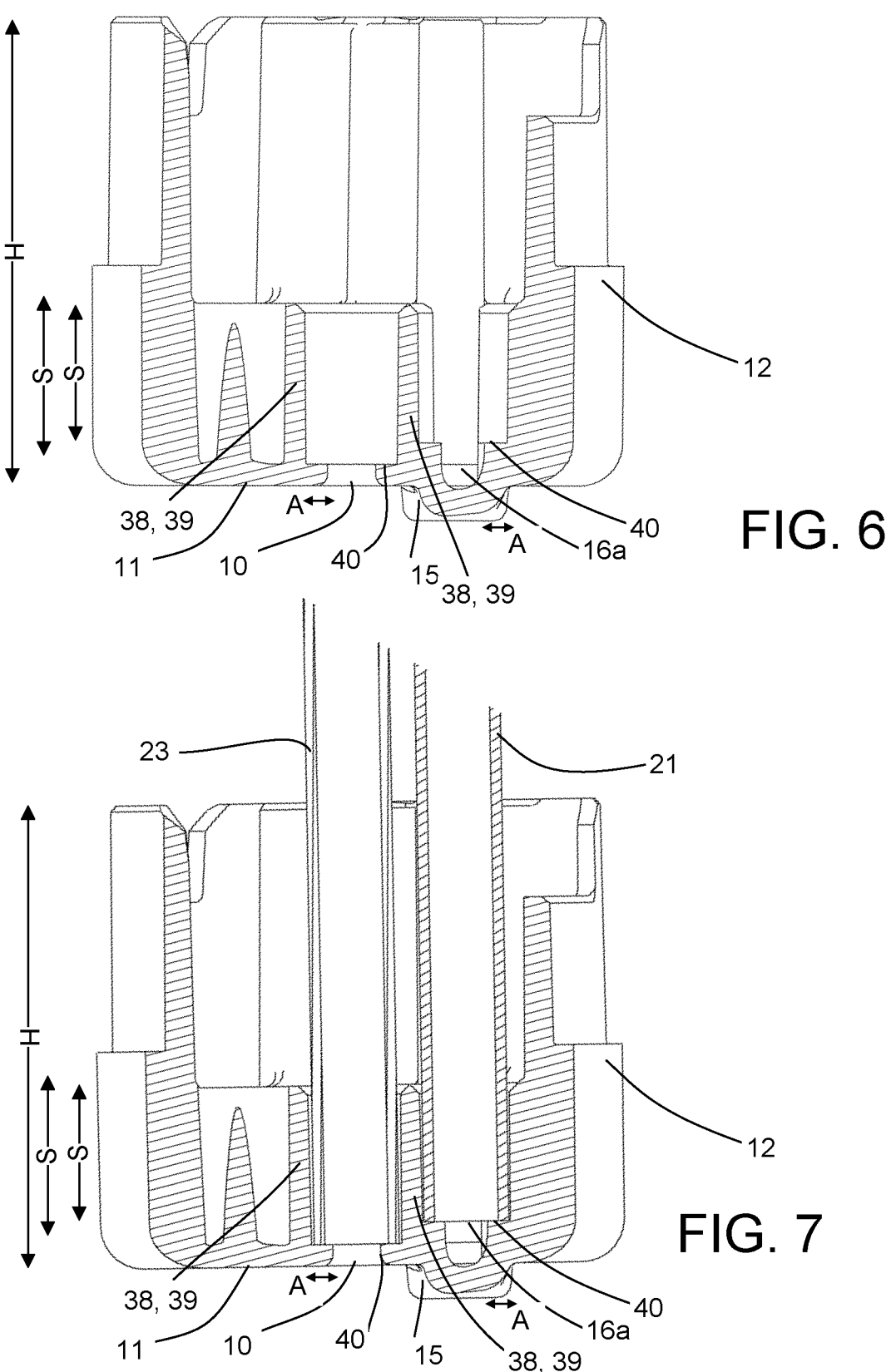
FIG. 6 shows a cross-sectional view of the tip part of FIG. 2 taken along the line B-B in FIG. 3.
FIG. 7 shows the cross-sectional view of the tip part of FIG. 6 with inserted tubes.
Figures 8, 9:
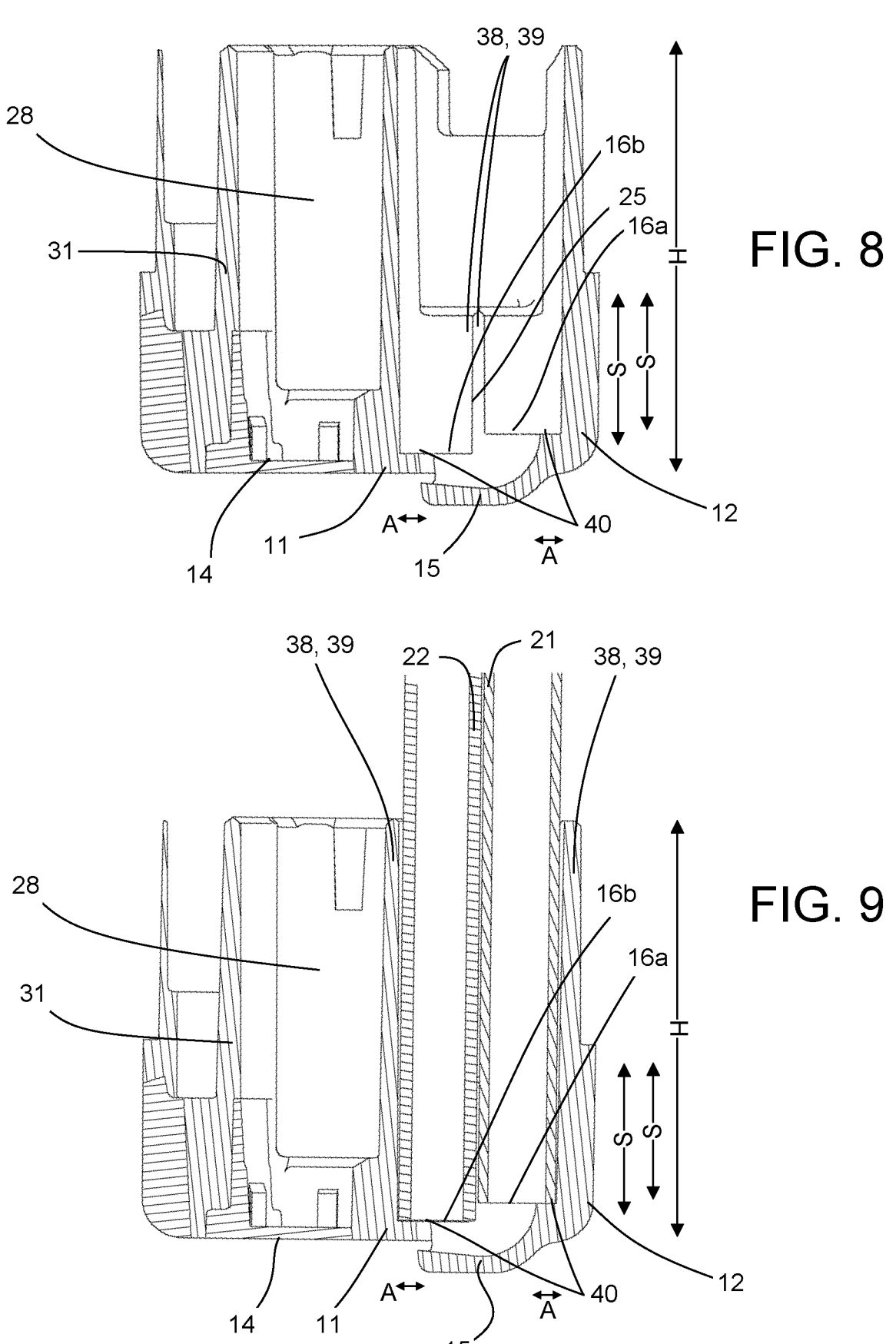
FIG. 8 shows a cross-sectional view of the tip part of FIG. 2 taken along the line C-C in FIG. 3.
FIG. 9 shows the cross-sectional view of the tip part of FIG. 8 with inserted tubes.
Figures 10, 11:
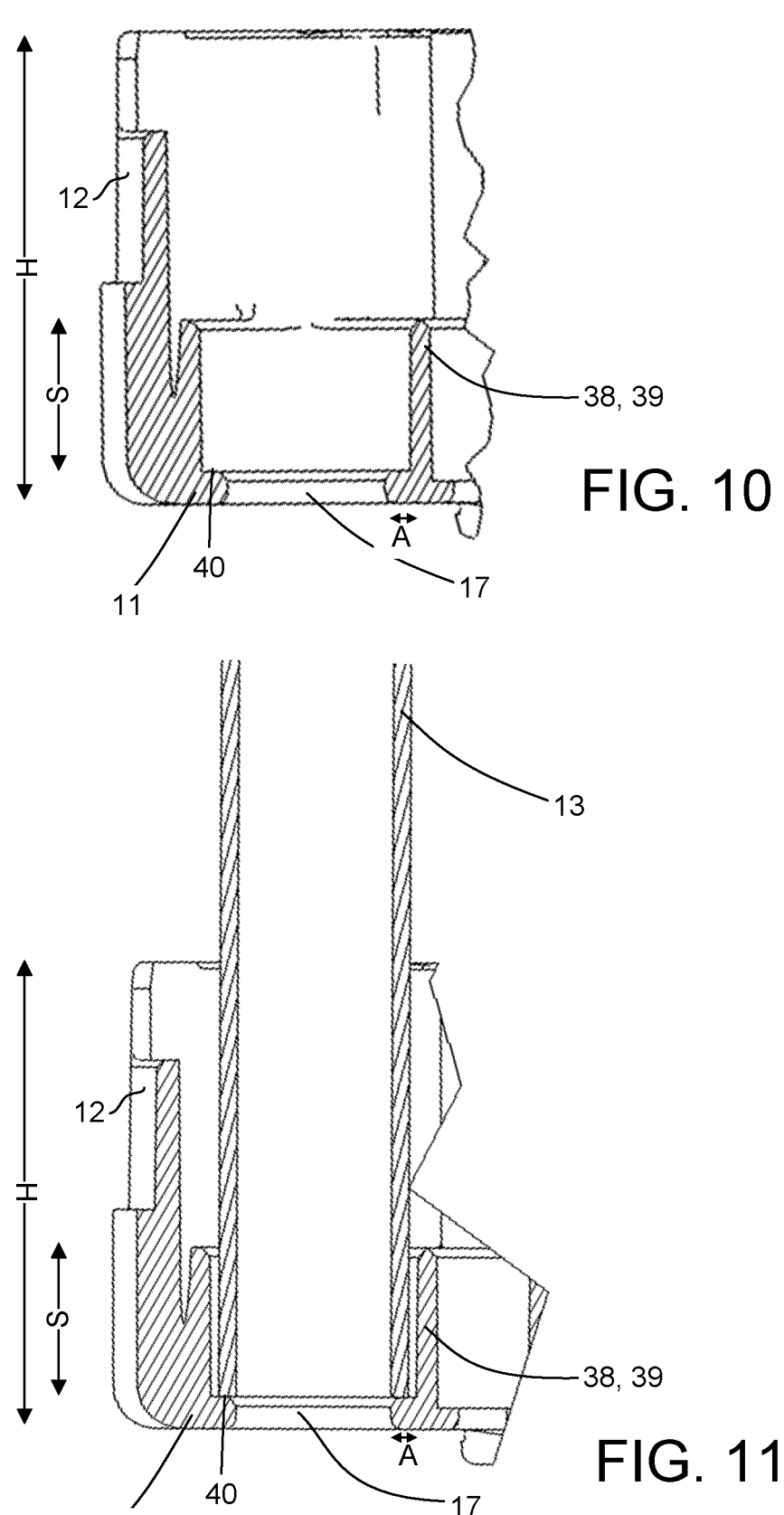
FIG. 10 shows a cross-sectional view of the tip part of FIG. 2 taken along the line D-D in FIG. 3.
FIG. 11 shows the cross-sectional view of the tip part of FIG. 10 with inserted tube.
Figure 12:
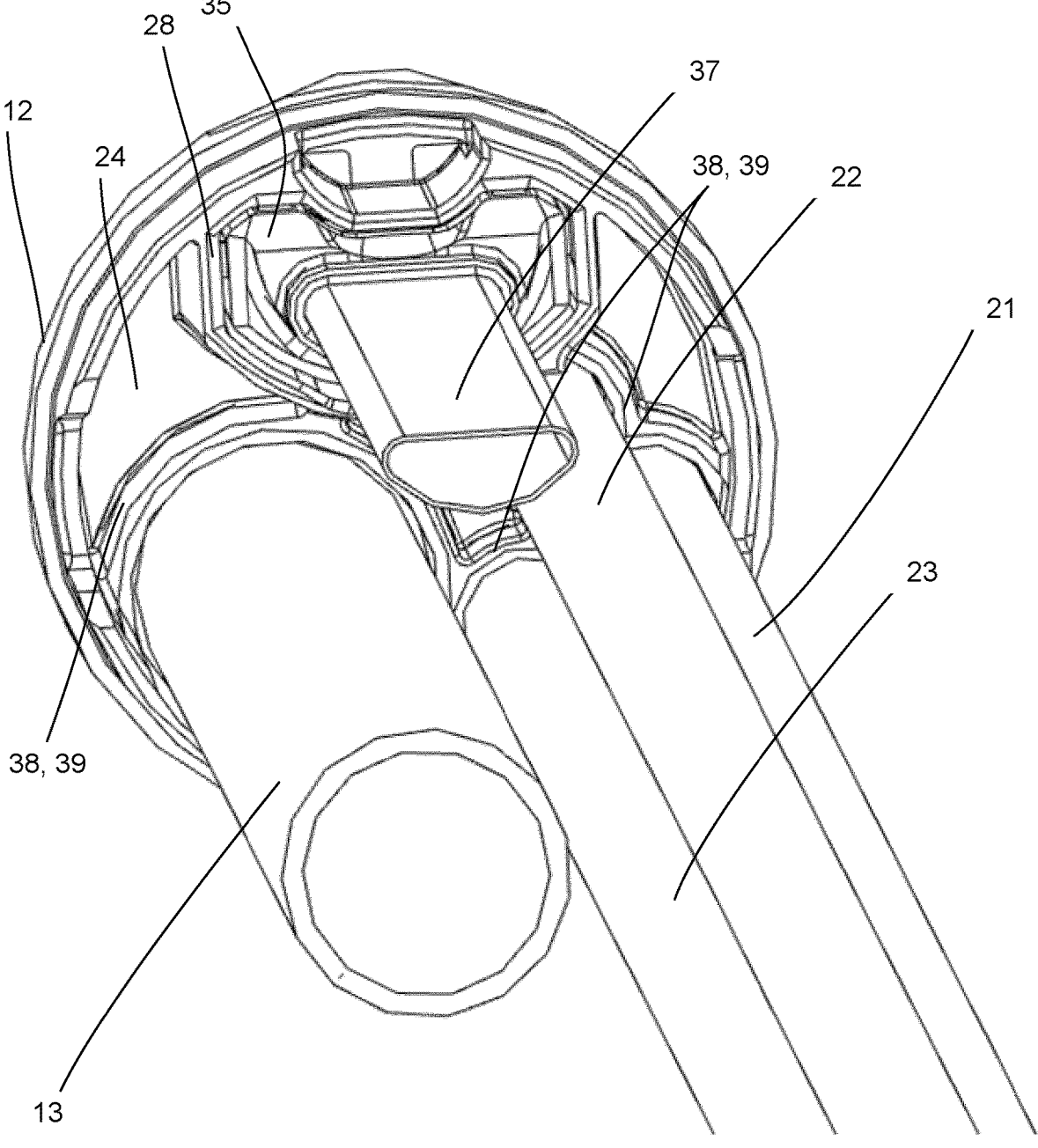
FIG. 12 shows a rear perspective view of the tip part of FIG. 2 with inserted camera assembly and tubes.

As best seen in FIG. 4, the circumferential tube sleeve walls 39 of two of the tube insertion sleeves 38 are partly formed by and coinciding with the circumferential tube sleeve walls 39 of two other tube insertion sleeves 38.

In a development of the previous embodiment, the circumferential tube sleeve wall 39 of one of tube insertion sleeves 38 is partly formed by and coinciding with the circumferential tube sleeve walls 39 of two other tube insertion sleeves 38 and also at least partly formed by and coinciding with the circumferential housing wall 12. In an embodiment, the tip part further comprises a camera insertion sleeve according to any one of the preceding claims, wherein at least one two of the tube insertion sleeves are partly formed by and coinciding with the circumferential camera sleeve wall 31.

After manufacture of the tip part 2, the tubes are inserted into the tube insertion sleeves 38 through the proximal end of the tube insertion sleeves until a distal end of the tubes 13, 21, 22, 23 abuts the tube abutment surface 40, whereby the distal end of the tubes 13, 21, 22, 23 is positioned to allow fluid flow through the tube 13, 21, 22, 23 to and through the fluid openings 10, 16*a*, 16*b*, 17. An adhesive and sealant is then provided between a distal end of the tubes 13, 21, 22, 23 and the abutment surfaces 40, and between an interior surface of the tube insertion sleeves 38 and an exterior surface of the tubes 13, 21, 22, 23.

The tip part 2 is manufactured by an embodiment of the methods according to this disclosure as described in the following.

First, the front wall 11, the circumferential wall 12, the camera window 14, the nozzle 15, the camera insertion sleeve 28, and the tube insertion sleeves 38 are molded in one piece with each other by means of injection molding in a two-component molding process. A suitable molding tool is provided, and the first polymer material in melted or molten form is introduced into the molding tool. The second polymer material on a melted form is then introduced into the molding tool. The first and second materials are then allowed to set and form an integral component in one unit or one piece. This one piece is then removed or extracted from the molding tool. The molding tool comprises a first cavity, a second cavity, and a core. The first material is allowed to set or partly set before the second material is introduced. As mentioned, the second material is transparent, and it is introduced under higher pressure than the first material. The second material forms the camera window 14, which constitutes only a minor part of the total material of the exterior housing 9. The first material is opaque at least in its set form.

Then, components including the tubes 21, 22, 13*a* and the camera assembly 27 are inserted in the tube insertion sleeves 38 and camera insertion sleeve respectively in the interior spacing 24 of the exterior housing 9.

Hereby, the exterior housing 9, including the nozzle 15, camera insertion sleeve 28, tube insertion sleeves 38 and the camera window 14, can be manufactured automatically in one single working procedure or working step by means of the two-component injection molding process as described, which saves time and costs in manufacture of the tip part 2. The tubes 13, 21, 22, 23 can then easily be positioned in the tube insertion sleeves 38, and further components, such as the camera assembly 27 can then be inserted in to the camera insertion sleeve 28 positioned within the interior spacing 24 of the exterior housing 9.

LIST OF REFERENCE NUMERALS

1 Endoscope
2 Tip part
3*a* Distal end
3*b* Proximal end
4 Insertion tube
4*a* Outer sheath
5 Handle
6 Working channel inlet

7 Bending section
8 Fluid hose
9 Exterior housing
9*a* Open proximal end
10 Rinsing fluid opening
11 Distal front wall
12 Circumferential housing wall
12*b* Step
13 Working channel tube
14 Camera window
14*a* Exterior surface
15 Nozzle
16*a* liquid fluid opening
16*b* gas fluid opening
17 Working channel fluid opening
18 Camera window part
19 Light window part
20 Light guide
21 Liquid tube
22 Gas tube
23 Rinsing fluid tube
24 Interior spacing
25 Slot
26 Display
27 Camera assembly
28 Camera insertion sleeve
28*a* Proximal end
29 Vision sensor
30 Light source
31 Circumferential camera sleeve wall
38 Tube insertion sleeve
39 Circumferential tube sleeve wall
40 Tube abutment surface
42 Control lever
43, 44 Control knobs
45 Combined image processing and fluid supply unit
46 Fluid control dials

The invention claimed is:

1. An endoscope comprising:

a tube having a distal end;

a housing including:

an open proximal end and a distal end, a tube insertion sleeve comprising an inner surface and an outer surface, a distal front wall comprising a camera window and a proximal surface, and a circumferential housing wall comprising an outer surface and an inner surface, the tube insertion sleeve, the distal front wall and the circumferential housing wall being integrally formed in one piece, the tube insertion sleeve at least partly formed by or coinciding with the circumferential housing wall, the circumferential housing wall extending a total housing length in a proximal direction from the distal front wall to the proximal end of the housing, the distal front wall and the circumferential housing wall enclosing an interior spacing of the housing; and a camera assembly configured to provide an image, the camera assembly positioned proximally of the proximal surface of the distal front wall, wherein the tube insertion sleeve comprises an open proximal end and a distal end, the distal end being connected to and extending proximally from the proximal surface of the distal front wall;

wherein the distal front wall has a fluid opening which is aligned with the distal end of the tube insertion sleeve, the proximal surface of the distal front wall surrounding the fluid opening to provide a tube abutment surface, the outer surface of the tube insertion sleeve extending from the inner surface of the circumferential housing wall with portions of the interior spacing being between the outer surface of the tube insertion sleeve and the inner surface of the circumferential housing wall;

wherein the distal end of the tube is positioned inside the tube insertion sleeve with the distal end of the tube next to or abutting the tube abutment surface, and whereby a fluid flowing through the tube can be discharged through the fluid opening of the distal front wall.

2. The endoscope of claim 1, wherein the tube insertion sleeve is fluid tight and/or fluid sealed from a surrounding portion of the interior spacing.

3. The endoscope of claim 1, wherein a total tube sleeve length of the tube insertion sleeve extends from the proximal surface of the distal front wall to the proximal end of the tube insertion sleeve, wherein the total tube sleeve length is less than the total housing length.

4. The endoscope of claim 3, wherein the tube abutment surface is positioned equal to or less than $3/10$ of the total housing length from a distal end surface of the distal front wall in the distal-proximal direction.

5. The endoscope of claim 1, wherein the distal end of the tube abuts the tube abutment surface.

6. The endoscope of claim 5, wherein the tube is fluid sealed against the tube insertion sleeve by an adhesive and/or a sealant.

7. The endoscope of claim 6, wherein the adhesive and/or the sealant is provided between the abutment surface and the tube to form a fluid seal between the distal end of the tube and the tube abutment surface.

8. The endoscope of claim 1, wherein an adhesive and/or a sealant is provided between an interior surface of the tube insertion sleeve and the tube.

9. The endoscope of claim 1, the endoscope further comprising a second tube, wherein the housing further comprises a second tube insertion sleeve and a camera insertion sleeve, the camera insertion sleeve including an inner surface and an outer surface, wherein the camera b y is positioned in the camera insertion sleeve, wherein the tube insertion sleeve is at least partly formed by and/or coinciding with the camera insertion sleeve, wherein the second tube insertion sleeve comprises an inner surface and an outer surface extending from a proximal end to a distal end of the second tube insertion sleeve, and wherein the second tube insertion sleeve is at least partly formed by or coinciding with the circumferential housing wall and at least partly formed by or coinciding with the tube insertion sleeve.

10. The endoscope of claim 9, wherein the housing comprises a third tube insertion sleeve, and wherein the third tube insertion sleeve is at least partly formed by or coinciding with the tube insertion sleeve and the second tube insertion sleeve.

11. The endoscope of claim 10, wherein the third tube insertion sleeve is at least partly formed by or coinciding with the circumferential housing wall.

12. The endoscope of claim 1, further comprising a camera insertion sleeve, the camera insertion sleeve including an inner surface and an outer surface, wherein the camera assembly is positioned in the camera insertion sleeve, and wherein the tube insertion sleeve is at least partly formed by and/or coinciding with the camera insertion sleeve.

13. A method of manufacture the endoscope of claim 1, the method comprising:

inserting the tube into the tube insertion sleeve through the proximal end of the tube insertion sleeve until the distal end of the tube abuts or is next to the tube abutment surface, whereby a fluid flowing through the tube can be discharged through the fluid opening.

14. The method of claim 13, further comprising providing an adhesive and/or a sealant between the distal end of the tube and the abutment surface.

15. The method of claim 13, further comprising providing an adhesive and/or a sealant between an interior surface of the tube insertion sleeve and an exterior surface of the tube.

16. A system comprising:

the endoscope of claim 1; and a display for displaying an image provided by the camera assembly.

17. The endoscope of claim 1, wherein the housing further comprises:

a camera insertion sleeve;

a second tube insertion sleeve;

a third tube insertion sleeve comprising a distal fluid opening;

a fourth tube insertion sleeve comprising a distal fluid opening; and a nozzle, wherein the camera assembly is positioned in the camera insertion sleeve, wherein the distal fluid opening of the third tube insertion sleeve and the distal fluid opening of the fourth tube insertion sleeve are configured to discharge fluids into the nozzle, wherein the tube insertion sleeve is at least partly formed by and/or coinciding with the camera insertion sleeve, wherein the second tube insertion sleeve is at least partly formed by or coinciding with the tube insertion sleeve, and wherein a portion of the interior spacing is located between the tube insertion sleeve, the second tube insertion sleeve, and the camera insertion sleeve.

18. The endoscope of claim 17, wherein the third tube insertion sleeve is at least partly formed by or coinciding with the fourth tube insertion sleeve.

19. The endoscope of claim 17, wherein the third tube insertion sleeve and the fourth tube insertion sleeve extend side-by-side and comprise a longitudinal slot between them.

20. A system comprising:

the endoscope of claim 17; and a display for displaying an image provided by the camera assembly.

21. The endoscope of claim 1, wherein the camera insertion sleeve is closed off by the camera window at a distal end of the camera insertion sleeve and comprises a proximal opening configured to insert the camera assembly into the camera insertion sleeve.

* * * * *